(12) United States Patent
Watanabe

(10) Patent No.: US 6,428,206 B1
(45) Date of Patent: Aug. 6, 2002

(54) X-RAY DIAGNOSTIC IMAGING APPARATUS

(75) Inventor: Naoto Watanabe, Tochigi-ken (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/502,000

(22) Filed: Feb. 11, 2000

(30) Foreign Application Priority Data

Feb. 12, 1999 (JP) .............................................. 11-034845

(51) Int. Cl.[7] .................................................. H05G 1/02
(52) U.S. Cl. ........................................................ 378/197
(58) Field of Search ................................. 378/195–197

(56) References Cited

U.S. PATENT DOCUMENTS 5,410,584 A * 4/1995 Schaefer et al. ............. 378/196
5,818,898 A   10/1998 Tsukamoto et al.
6,031,888 A * 2/2000 Ivan et al. ................... 378/196

* cited by examiner

Primary Examiner—Craig E. Church
(74) Attorney, Agent, or Firm—Oblon, Spivak, McClelland, Maier & Neustadt, P.C.

(57) ABSTRACT

Provides an X-ray diagnostic imaging apparatus that makes it possible to pick up images of a subject under examination at accurate and a variety of positions thereby to improve the operation of an operator and that realizes a simple and compact structure of the apparatus. This X-ray diagnostic imaging apparatus comprises an X-ray generator for irradiating X-rays onto the subject, an X-ray detector for taking in an X-ray image formed by the X-rays irradiated by the X-ray generator onto the subject and transmitted through the subject, an arm extended from the X-ray generator to make a detour around the subject, for holding the X-ray detector, and holders for movably holding the X-ray generator. The X-ray generator and the X-ray detector are formed integrally by the arm, and the X-ray generator is held and driven by the holders.

18 Claims, 16 Drawing Sheets

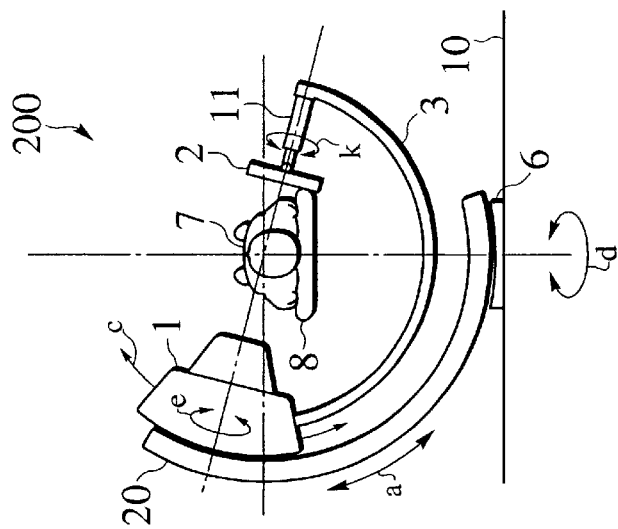
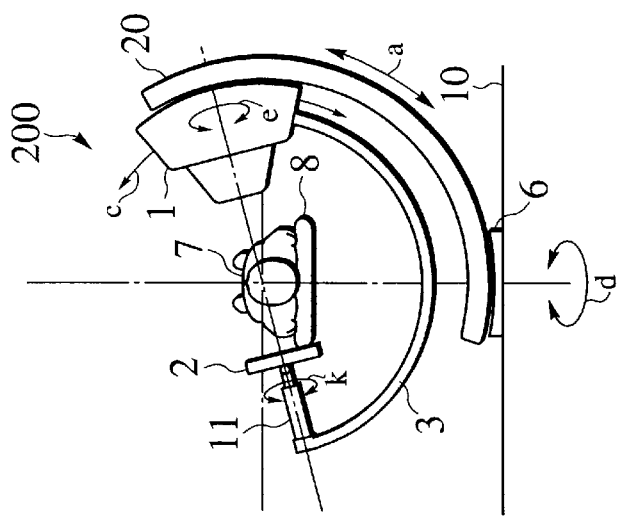
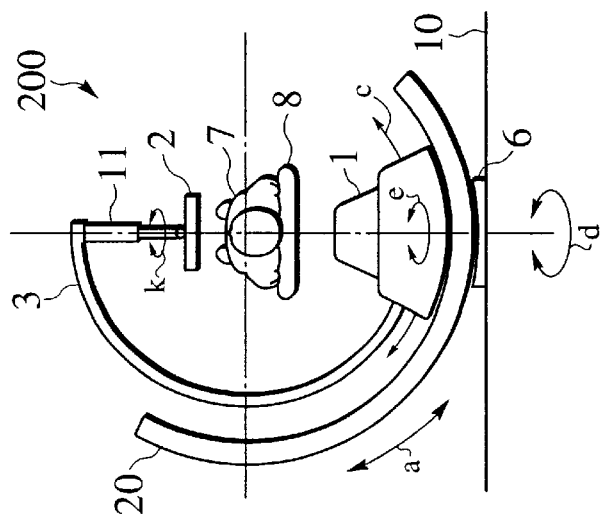

X-RAY DIAGNOSTIC IMAGING APPARATUS

BACKGROUND OF THE INVENTION

1. Field of the Invention

The present invention relates to an X-ray diagnostic imaging apparatus. The present invention particularly relates to a technique for making it possible to pick up images of a human body or a subject under examination at accurate and a variety of image pick-up positions, for improving the operation of an operator, and for achieving a provision of a compact and simple structure of an X-ray diagnostic imaging apparatus, in diagnosing the subject based on an image obtained by irradiating radial rays such as X-rays, for example, onto the subject.

2. Description of the Background Art

An X-ray diagnostic imaging apparatus irradiates radiation such as X-rays, for example, onto a subject under examination, and detects a distribution of the radiation transmitted through the subject, thereby to pick up an image of a detected portion of the subject. As a supporting unit in this X-ray diagnostic imaging apparatus, there is a circulator supporting unit, for example.

FIG. 1 is a schematic view for showing a conventional X-ray diagnostic imaging apparatus. As shown in FIG. 1, in this X-ray diagnostic imaging apparatus, an X-ray generator 1 and an X-ray detector 503 are arranged to face each other on both ends of an arm 501, and they are supported in a fixed state. As shapes of the arm 501, there have been known two broad types of a C-type and a U-type. From the viewpoint of the efficiency of a three-dimensional positioning, the C-type as shown in FIG. 1 has been used as the main. The arm 501 is held slidably by a holder 502. The holder 502 is held rotatably around a main axis by a supporting pillar (not shown), and the supporting pillar is installed rotatably around the supporting pillar on the ceiling or on the floor. A supporting pillar of the type suspended from the ceiling has a rail fixed to the ceiling, and the supporting section can make a horizontal move in one direction or two directions along this rail.

As the X-ray detector 503, an image intensifier (hereinafter to be referred to as an I.I.) is employed. The X-ray detector 503 converts X-ray information of the X-rays transmitted through the subject 7 into optical information, and collects the optical information with an optical lens and takes it into a TV camera. The information taken into the TV camera is displayed as an image. The X-ray detector 503 can be moved by a moving mechanism to upward and downward directions with respect to the X-ray generator 1 shown in FIG. 1.

The above conventional X-ray diagnostic imaging apparatus, however, has had the following problems.

First, according to the conventional X-ray diagnostic imaging apparatus, articles of heavy weight, such as, for example, the I.I., the optical system mechanism, the X-ray detector 503 such as the TV camera, and the X-ray generator 1, are provided on both ends of the C-type arm 501. Accordingly, when the arm 501 having a large size and a heavy weight is rotated in a direction of the main axis, there is generated a large rotation inertia, making it difficult to fine tune a rotation angle of the arm 501. Therefore, it has been difficult to achieve a correct control of an image pick-up position intended by the operator.

Thus, in order to facilitate a fine-tuned control of an image pick-up position, it may be considered appropriate to reduce the size and weight of the X-ray detector 503, by using a solid detector formed by a plurality of solid image pick-up elements, in place of the I.I. However, when this solid detector is used, a weight balance between the X-ray detector and the X-ray generator 1 may be lost, and the rotation inertia moment may become substantially worse than the current situation, which makes it difficult to carry out the fine-tuned control.

On the other hand, in recent years, there have been made trials to obtain a three-dimensional image of a subject under examination by picking up images of the subject while rotating the C-type arm, and then by reconstructing projection images of the subject into a three-dimensional image. In order to reconstruct a three-dimensional image, it is necessary to obtain projection images of the subject corresponding to at least 180 degrees plus X-ray cone beam (or fan beam) angle. However, the conventional C-type arm 501 and the holder 502 have a limit to their slide strokes, and, therefore, it is difficult to obtain image information that can provide a three-dimensional reconstruction.

For collecting image information from the plurality of angles, according to the conventional X-ray diagnostic imaging apparatus, it is possible to rotate the C-type arm 501 around the main axis. However, in this case, in order to avoid an interference generated between the arm 501 and the subject 7 at the time of the rotation, there is no other way than to rotate the subject 7 around a body axis L of the subject by making an access to the subject 7 from a head side. This method has a limitation to an area of the subject 7 to which X-rays are irradiated and from which transmitted X-rays can be collected. In other words, as the conventional arm 501 access from the head side of the subject 7, a move of the arm 501 in the direction of the body axis L is limited to a range in which the head of the subject 7 and the arm 501 are not brought into contact with each other. Accordingly, it has been difficult to access to a lower body part of the subject 7, particularly, to an inguinal region, for example. As a result, it has been difficult to control image pick-up positions in various ways in line with an operator's intention.

Further, as a large mechanism is required for the supporting unit for supporting the holder 502 and the arm 501 that are necessary for collecting the image of the main axis rotation, the conventional the X-ray diagnostic imaging apparatus has taken a large installation space, which interferes with the field of vision of an operator and interrupts his or her operation.

SUMMARY OF THE INVENTION

It is an object of the present invention to provide an X-ray diagnostic imaging apparatus capable of easily collecting images at accurate and a variety of image pick-up positions, by improving an access of an X-ray generator and an X-ray detector to a subject under examination.

It is another object of the present invention to provide an X-ray diagnostic imaging apparatus capable of improving the operation of an operator without interfering with the field of vision of the operator, through the reduction in size and weight of a supporting unit.

In order to achieve the above objects, a first aspect of the present invention provides, as shown in FIG. 2, an X-ray diagnostic imaging apparatus 100 for irradiating X-rays onto a subject under examination and picking up an image of the subject by detecting the X-rays transmitted through the subject, the X-ray diagnostic imaging apparatus comprising: an X-ray generator 1 for irradiating X-rays onto the subject; an X-ray detector 2 for taking in an X-ray image formed by the X-rays irradiated onto the subject and transmitted through the subject; an arm 3 extended from the X-ray generator 1 to make a detour around the subject, for holding the X-ray detector 2; and a holder 4 and 5 for movably holding the X-ray generator 1.

According to the above structure, the X-ray generator 1 and the detector 2 are formed integrally with the arm 3, and the X-ray generator 1 is held and driven by the holders 4 and 5. Accordingly, the arm 3 that holds the X-ray generator 1 and the detector 2 by itself does not require a driving mechanism. Further, it is not necessary to have a space for installing the mechanism for carrying out a main axis rotation. Thus, it is possible to provide a simpler and lighter-weight structure of the X-ray diagnostic imaging apparatus. Further, unlike the conventional apparatus, it is not necessary to take into consideration the maintenance of a balance between the X-ray generator and the detector and the rotation inertia generated during a rotation of the holder. Therefore, it becomes possible to accurately control an image pick-up position.

The X-ray generator 1 may be provided in the holders 4 and 5 so as to be rotatable with the X-ray irradiation direction as an axis. Further, the X-ray generator 1 may also be provided so as to be slidable along the inner surface of the holders 4 and 5.

The holders 4 and 5 may be formed in arc shapes, and the X-ray generator 1 may be provided so as to be slidable along the arcs of the holders 4 and 5.

The holders 4 and 5 may be supported rotatably by a supporting base 4. Further, the holders 4 and 5 may be supported by the supporting base 6 so as to be slidable along the arcs of the holders 4 and 5.

The supporting base 6 may be provided movably.

The holders may not be two, but only one holder may be provided like a holder 20 shown in FIG. 10. Alternatively, the holder may be structured by a first holder 4, formed in an arc shape, for movably holding the X-ray generator, and a second holder 5 for supporting the first holder slidably along the arc of the first holder.

The X-ray detector 2 may be structured by a planar detector formed by a two-dimensional array of a plurality of X-ray detecting elements for converting X-rays transmitted through the subject into charge signals and for storing the charge signals.

The X-ray detector 2 may be held by the arm 3 in such a way as to be able to change a distance from the X-ray detector 2 to the X-ray generator 1. Further, the X-ray detector 2 may be held by the arm 3 rotatably around an X-ray axis formed by a line connecting between the X-ray generator 1 and the X-ray detector 2. Further, the X-ray detector 2 may also be held by the arm 3 so that an angle formed by the X-ray detector 2 and the X-ray generator 1 can be changed.

A second aspect of the invention provides, an X-ray diagnostic imaging apparatus for irradiating X-rays onto a subject under examination and picking up an image of the subject by detecting the X-rays transmitted through the subject, the X-ray diagnostic imaging apparatus comprising: an X-ray generator 1 for irradiating X-rays onto the subject; an X-ray detector 2 for taking in an X-ray image formed by the X-rays irradiated onto the subject and transmitted through the subject, the X-ray detector 2 being structured by a two-dimensional array of a plurality of X-ray detecting elements for converting X-rays transmitted through the subject into charge signals and for storing the charge signals; an arm 3 extended from the X-ray generator 1 to make a detour around the subject, for fixedly holding the X-ray detector 2; and at least one holder 4 and 5 for holding the X-ray generator 1 so that the X-ray generator 1 can rotate and/or slide along the holder.

According to the above-described structure, the X-ray generator 1 is provided rotatably or slidably along the holder 4, and the holder 5 is supported movably or slidably by the supporting base 6. Further, the holder is structured by the first holder 4 and the second holder 5 that can slide along each other, and the X-ray detector 2 is provided movably in forward and backward directions or is tilted. With this structure, making an access to the subject can be improved, and the operation of the operator can also be improved. Thus, it becomes possible to collect images of the subject over a wider range of the body.

Other features and advantages of the present invention will become apparent from the following description taken in conjunction with the accompanying drawings.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 9A to 9C are views for explaining a structure of an X-ray diagnostic imaging apparatus according to a second embodiment of the present invention;

DETAILED DESCRIPTION OF THE PREFERRED EMBODIMENTS

Embodiments of an X-ray diagnostic imaging apparatus according to the present invention will be explained in detail below with reference to FIG. 2 to FIG. 19.

First Embodiment

Next, a first embodiment of an X-ray diagnostic imaging apparatus according to the present invention will be explained with reference to FIG. 2 to FIG. 5.

Figure 2:
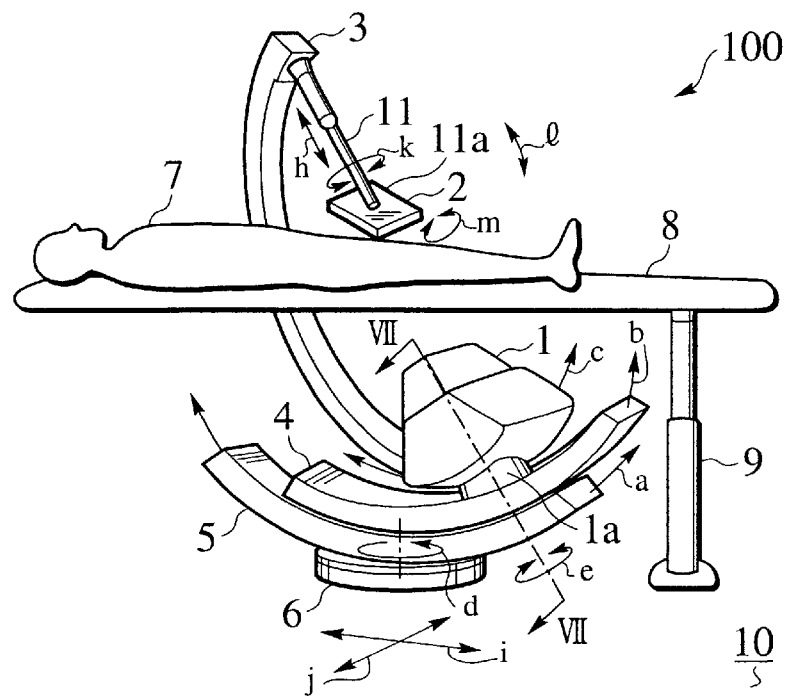
FIG. 2 is a perspective view for showing an outline of an X-ray diagnostic imaging apparatus according to a first embodiment of the present invention.
Figure 3:
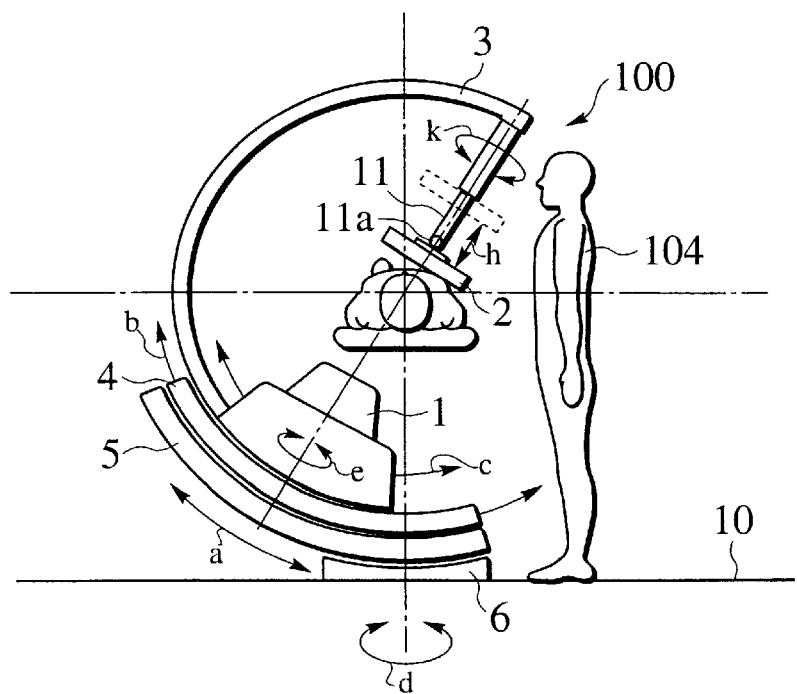
FIG. 3 is a front view of the X-ray diagnostic imaging apparatus shown in FIG. 2 as viewed from the head side of a subject.

FIG. 2 is a perspective view for showing an X-ray diagnostic imaging apparatus 100 according to the first embodiment. FIG. 3 is a front view of FIG. 2. The X-ray diagnostic imaging apparatus 100 is for irradiating radiation such as X-rays, for example, onto a subject under examination 7 by an X-ray generator 1 (a radiation generator), and detecting the X-rays transmitted through the subject 7 by an X-ray detector 2, thereby to pick up an image of a detected portion of the subject 7.

The X-ray diagnostic imaging apparatus 100 according to the first embodiment comprises first and second arms 4 and 5, an arm holder 6 for supporting the first and second arms 4 and 5, the X-ray generator 1 held by the first arm 4, the X-ray detector 2 disposed at an opposite side of the X-ray generator 1 by sandwiching the subject 7 therebetween, an a C-type arm 3 for holding the X-ray detector 2. In the first embodiment, the first and second arms 4 and 5 correspond to a holder, the arm holder 6 corresponds to a supporting base, and the C-type arm 3 corresponds to an arm, in claims, respectively.

In the first embodiment, the X-ray diagnostic imaging apparatus 100 is disposed on a floor 10 as well as being installed near a bed 8 for mounting the subject 7 thereon. The bed 8 is supported horizontally by a supporting pillar 9 installed on the floor 10, so as to be able to make a relative move with respect to the arm holder 6.

The first and second arms 4 and 5 are structured by members forming arc shapes of a quarter of a circle, for example, respectively. The first arm 4 directly holds the X-ray generator 1. The second arm 5 slidably holds the first arm 4 (as shown by reference a in FIG. 2), and is also slidably supported by the arm holder 6 (as shown by reference b in FIG. 2).

The arm holder 6 is embedded into the surface of the floor 10 rotatably around a vertical axis d. Further, according to the first embodiment, the arm holder 6 is installed on the floor 10 in such a way that the arm holder 6 can support the second arm 5 rotationally and slidably and can also slide in directions orthogonal with an irradiation direction of X-rays, that is, in i and j directions in FIG. 2. In other words, the arm holder 6 is provided on the floor so as to be able to make a two-dimensional move on the floor. Thus, the arm holder 6 can change its relative position with respect to the subject 7. For example, when the arm holder 6 slides in a direction of reference i in FIG. 2, the arm holder 6 can move to a body axial direction of the subject 7. Further, when the arm holder 6 slides in a direction of reference j in FIG. 2, the arm holder 6 can move in a direction orthogonal with a body axial direction of the subject 7.

The X-ray detector 2 can be structured by, for example, a solid image pick-up type planar detector structured by having photoelectric conversion elements laid out in a grid shape. A structure of the X-ray detector 2 formed by the planar detector will be explained in detail at a later stage.

The X-ray generator 1 is for irradiating X-rays onto the X-ray detector 2, and is provided rotatably on the first arm 4 (as shown by reference e in FIG. 2), by a rotation support 1a provided to be able to move by sliding along the first arm 4 (as shown by reference b in FIG. 2). The X-ray generator 1 and the X-ray detector 2 are connected to face each other by the C-type arm 3.

The C-type arm 3 is formed in a shape to make a detour around the subject 7 and the bed 8, for example, a semicircular shaped arc. The C-type arm 3 may have its one end fixed to the X-ray generator 1 to hold the X-ray generator, and have the other end thereof provided with an up-and-down moving mechanism 11 for holding the X-ray detector 2.

The up-and-down moving mechanism 11 moves the X-ray detector 2 in up and down directions (as shown by reference h in FIG. 2) to extend and withdraw the X-ray detector 2 to and from the subject 7, thereby to change a distance between the X-ray generator 1 and the X-ray detector 2. The up-and-down moving mechanism 11 may hold the X-ray detector 2 with a generally-known roller, rail or linear guide or the like, and may be driven with screws by transmitting a motor power to the screws through a belt or the like. Alternatively, a hydraulic expansion mechanism unit may be used.

The up-and-down moving mechanism 11 has a joint 11a provided at its front end for supporting the X-ray detector 2. The angle of the X-ray detector 2 can be adjusted by this joint 11a (as shown by reference m in FIG. 2). Further, the X-ray detector 2 is installed on the up-and-down moving mechanism 11 rotatably around a rotation direction of a radiation axis formed by connecting a line between the X-ray generator 1 and the X-ray detector 2 (as shown by reference k in FIG. 2).

Next, a structure of a circuit for constituting the above-described X-ray detector 2 by using a planar detector will be explained. This planar detector is disclosed in, for example, U.S. Pat. No. 5,818,898.

Flat panel X-ray detectors, which have an advantage of being capable of digitally X-ray imaging a human body under examination in real time, include (1) direct conversion detectors which convert incident X-rays directly into the electric charges and obtain electric signals and (2) indirect conversion planar detectors which convert incident X rays into light, convert the light into electric charges, and convert the electric charges into electric signals. An example of an indirect detector is disclosed in U.S. Pat. No. 4,689,487.

Figure 4:
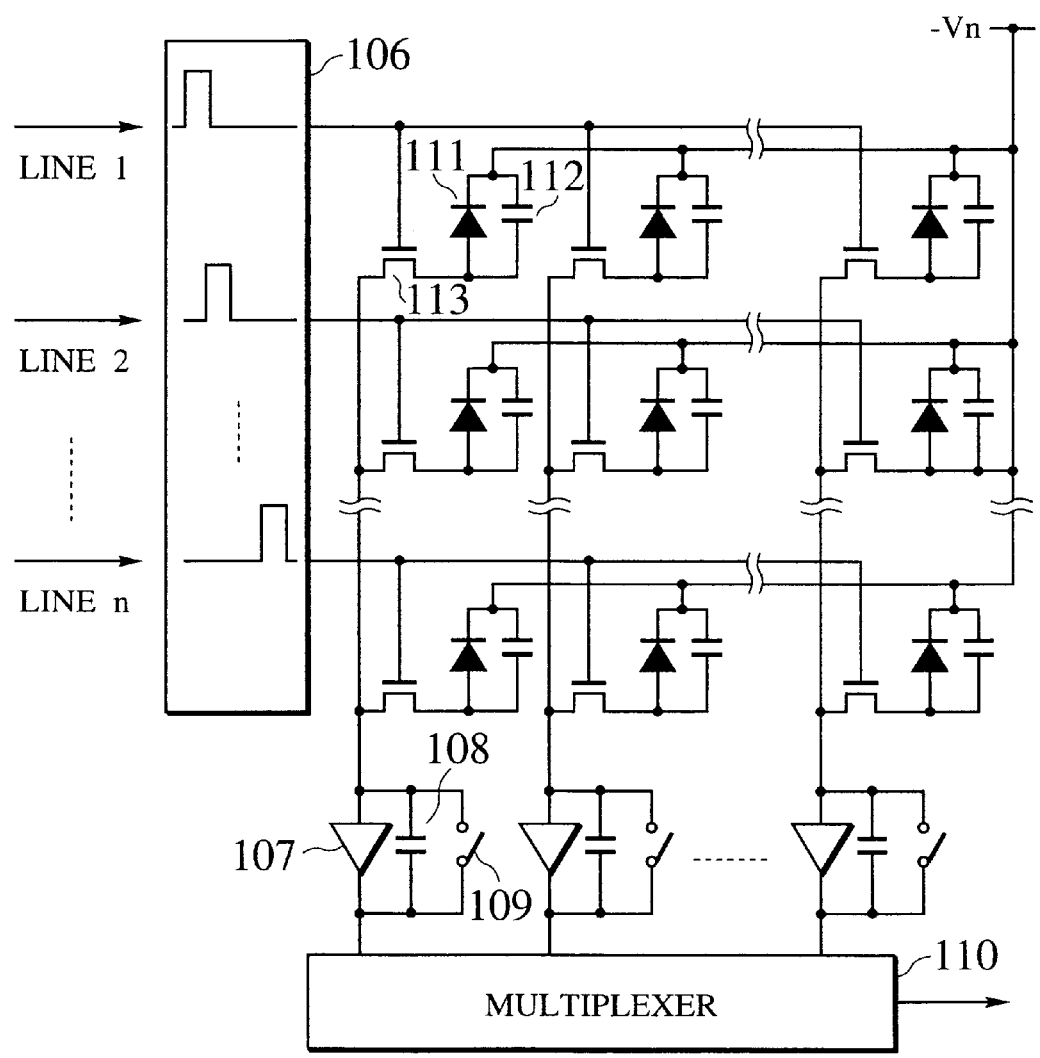
FIG. 4 is a view for showing exemplary circuit structure of a detector when a detector of the X-ray diagnostic imaging apparatus shown in FIG. 2 is structured with a planar detector.

As shown in FIG. 4, each detector element comprises a photodiode 111 which generates electric charges corresponding to the amount of incident light, a capacitor (hereinafter referred to as a storage capacitor) 112 for storing the charges from the photodiode, and a thin-film transistor (TFT) 113 serving as a switch used to read the charges stored on the storage capacitor.

The cathode of the photodiode 111 and one plate of the storage capacitor 112 are connected together to a reversebias power supply (−Vn), while the anode of the photodiode and the other plate of the storage capacitor are connected together to the source of the TFT 113.

Using each of the detector elements as one element, the flat panel X-ray detector 103 is constructed such that the elements are arranged in columns and rows (lines) to form a two-dimensional array. The gates of the respective TFT's 113 arranged in one line are connected together to a corresponding line output terminal of a gate driver 106.

From the line output terminals of the gate driver 106 control pulse signals which are output in the time sequence. Each of the TFT's 113 arranged in the same line is turned ON simultaneously by a corresponding control pulse signal. On the other hand, each of the TFT's arrange in the different lines is tuned ON in time sequence.

The drains of the respective TRT's 113 arranged in each column are connected together through an integration circuit which includes a readout amplifier 107, a capacitor (hereinafter referred to as a time-constant capacitor) 108, and a reset switch 109, to a corresponding one of input terminals of a multiplexer 110.

The multiplexer 110 is arranged to, during the duration of one pulse output from each line output terminal of the gate driver 106, sequentially provide signals applied to its inputs, one at a time, to its output.

Thus, when the TFT's arranged in one line are turned ON simultaneously by a control pulse signal output from a corresponding line output terminal of the gate driver 106, charges stored on the storage capacitors 112 are output through the corresponding respective TFT's 113 and then converted to voltages through the respective corresponding integration circuits. These voltages are sequentially output from the multiplexer 110 one at a time (on a pixel-by pixel basis). When the readout of one line is terminated in this manner, the readout of the next line is initiated. That is, like scanning lines of a television picture, the detector elements are sequentially read one at a time (pixel by pixel) for each line whereby image data (a video signal) for one frame is output.

Figure 5:
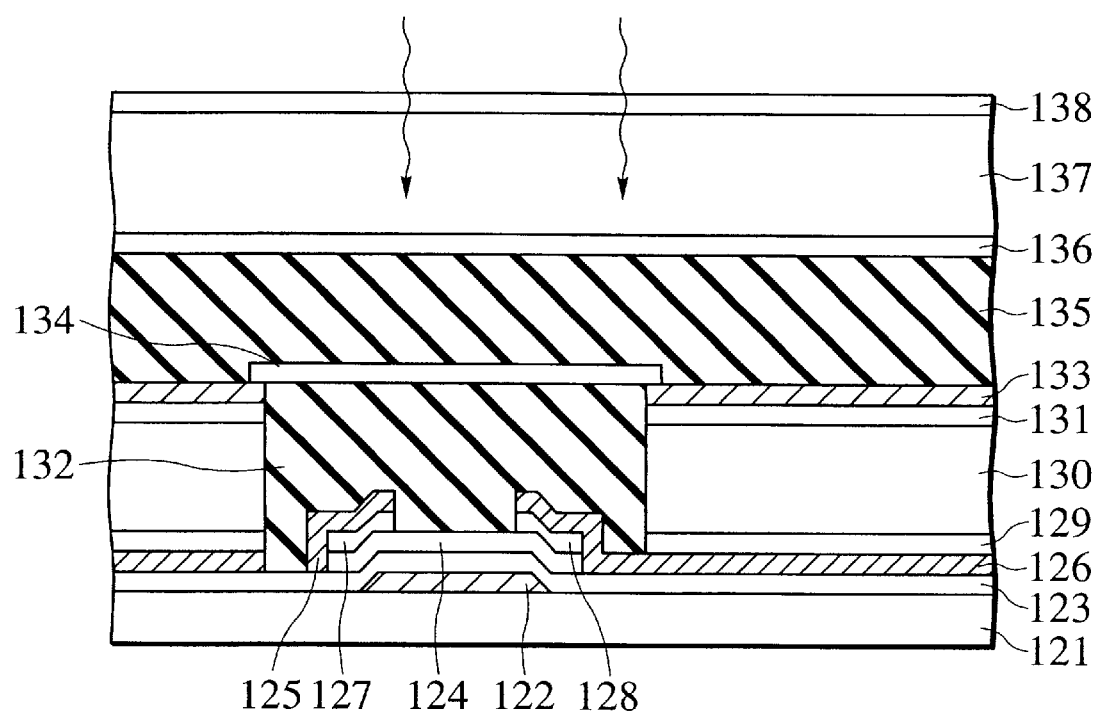
FIG. 5 is a sectional view of a detector element structure of a planar detector achieved by a semiconductor technique.

As shown in FIG. 5, a fluorescent layer that converts X rays to light is formed over the two-dimensional array of the detector elements. That is to say,a gate electrode 122 is formed in each TFT region on a substrate 121 and an SiNx layer 123 is formed on the gate electrode 122. In the TFT region, an a-Si layer 124, a drain electrode 125 and a source electrode 126 and the source electrode 126 are connected by the a-Si layer 124, not directly. In the gaps between the drain electrode 125, the source electrode 126 and the a-Si layer 124 are formed n+a-Si layers 127 and 128. Thus, a TFT is formed in the TFT region.

In each PD (photodiode) region on the substrate 121 an n+-type layer 129, an intrinsic (i-type) layer 130 and a p+-type layer 131 are formed on the SiNx layer 123 and the source electrode 126 form a photodiode 111 of the p-i-n structure.

A first polyimide layer 132 is formed over each TFT, and a transparent electrode 133 is formed over each photodiode 111. A metal electrode 134 is formed over the first polyimide layer 132 to connect the transparent electrodes 131 of the neighboring photodiodes together.

A second polyimide layer 135 is formed over the transparent electrode 133 and the metal electrode 134. A transparent protection layer 136, a fluorescent layer 137 and a light reflection layer 138 are formed over the second polyimide layer 135.

The method of obtaining an X-ray image will be described next. X-rays transmitted through a human body under examination are directed through the light reflection layer 138 onto the fluorescent layer 137. At this point, incident visible light is reflected by the light reflection layer 138; it is prevented from falling on the fluorescent layer 137.

By the fluorescent layer 137 the energy of incident X-rays is converted to the energy of visible light, which passes through the transparent protection layer 136, the second polyimide layer 135, and the transparent electrode 133 and is then received by the photodiode 111 that is sensitive to visible light.

The visible light is converted by the photodiode 111 to an electric charge, the amount of which is proportional to the energy of the visible light. The charge is stored on the storage capacitor 112. The stored charge is read out pixel by pixel for each line as described previously. The read signal is proportional to the energy of incident X-rays. By reconstructing signals read pixel by pixel, an X-ray image can be obtained.

Next, the operation of the X-ray diagnostic imaging apparatus according to the first embodiment will be explained with reference to FIGS. 6A to 6C, 7 and 8. In this case, a description will be made based on the assumption of a three-dimensional scan mode for reconstructing a three-dimensional image using image data picked up by an image pick-up system by rotating it around a subject over a range of 180 degrees plus α degrees.

Figure 6A:
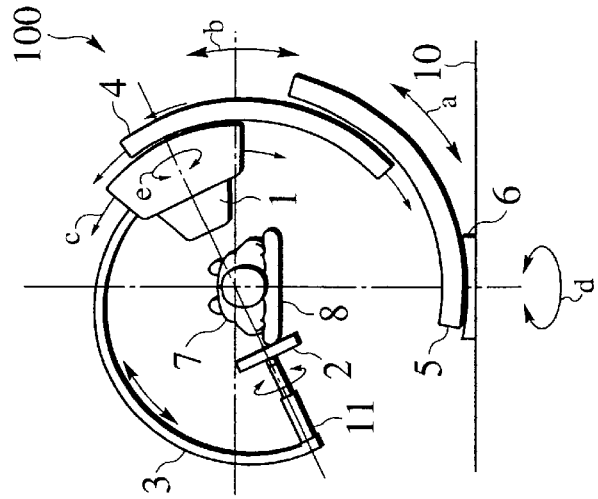
FIGS. 6A to 6C are views for explaining an operation of the X-ray diagnostic imaging apparatus shown in FIG. 2.

In an initial status shown in FIG. 6A, the first and second arms 4 and 5 are superimposed together on the arm holder 6 in a stationary status. The X-ray generator 1 is stationary at almost the center of the first arm 4. In this initial status, the X-ray generator 1 is positioned below the subject 7, and the X-ray detector 2 is positioned above the subject 7 so that both X-ray generator 1 and the X-ray detector 2 are oppositely disposed to sandwich the subject 7 therebetween.

Figure 6B:
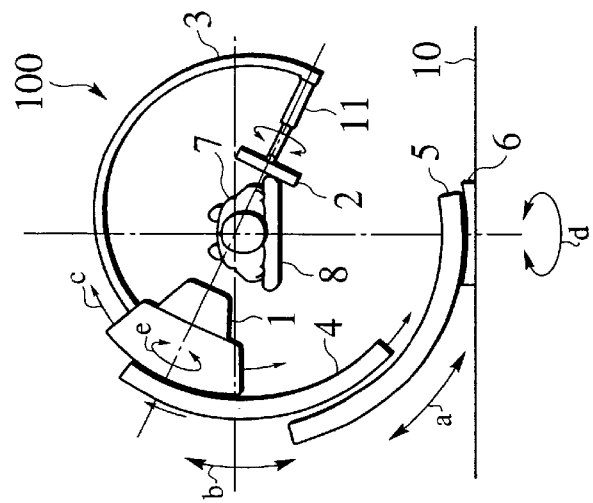

First, in the case of moving the detector 2 to the right half portion of the subject 7, the second arm 5 and the first arm 4 are slid respectively as shown (by reference a and reference b) in FIG. 6B, and the X-ray generator 1 is slid along the first arm 4 (as shown by reference c in FIG. 6B). Thus, the X-ray generator 1 is moved in a clockwise circumferential direction.

Figure 6C:
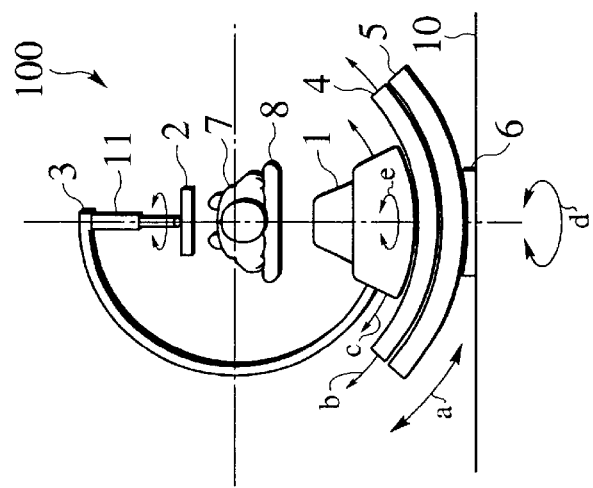

On the other hand, in the case of moving the detector 2 to the left half portion of the subject 7, the second arm 5 and the first arm 4 are slid respectively as shown (by reference a and reference b) in FIG. 6C, and the X-ray generator 1 is slid along the first arm 4 (as shown by reference c in FIG. 6C). Thus, the X-ray generator 1 is moved in a counterclockwise circumferential direction.

Figure 1:
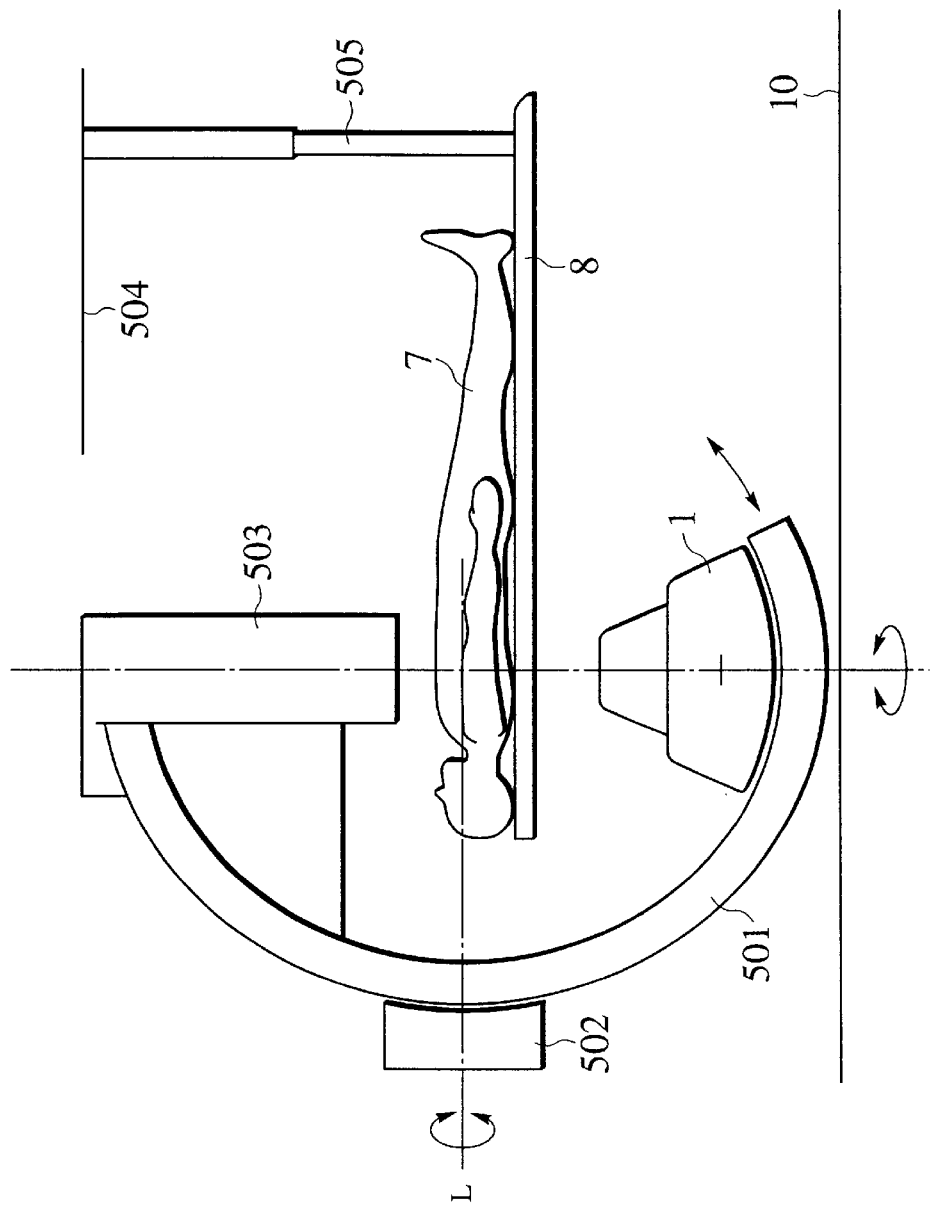
FIG. 1 is a view for explaining an outline of a circulator holder in an X-ray diagnostic imaging apparatus according to a conventional technique.

FIGS. 6A to 6C illustrate an example of the case where the first and second arms 4 and 5 are disposed to be orthogonal with a direction of a body axis of the subject 7, that is, in a lateral disposition for accessing to the C-type arm 3 from the side portion of the subject 7. However, the disposition is not limited to this. It is also possible to dispose the first and second arms 4 and 5 so as to be in parallel with the body axis, by rotating the arm holder 6 with its radial direction as an axis, that is, in a vertical disposition for accessing to the C-type arm 3 from the head portion of the subject 7, like the case as shown in FIG. 1. In this case, it is possible to rotate the X-ray image pick-up system in a body axial direction, by sliding the first arm 4 and the X-ray generator 1 along the second arm 5. Further, it is possible to obtain a complex angle setting by combining a rotation of the arm holder 6 and rotations of the first and second arms 4 and 5 and the X-ray generator 1.

In the case of observing an inguinal region or a lower extremity of the subject 7, the bed 8 mounted with the subject 7 is moved to the head side, or the arm holder 6 is moved to a body axial direction (as shown by reference i in FIG. 2) before irradiating X-rays onto the subject 7. In this case, when the X-ray generator 1 is rotated with its radial direction as an axis (as shown by reference e in FIG. 2), if needed, it is possible to avoid an interference between the C-type arm 3 and the subject 7 or the bed 8.

Further, when the up-and-down moving mechanism 11 is expanded or contracted and also when the angles in two directions of the X-ray detector 2 are adjusted by the rotary mechanism (joint) 11a, the X-ray detector 2 can be brought into a close contact with the subject 7.

Figure 7:
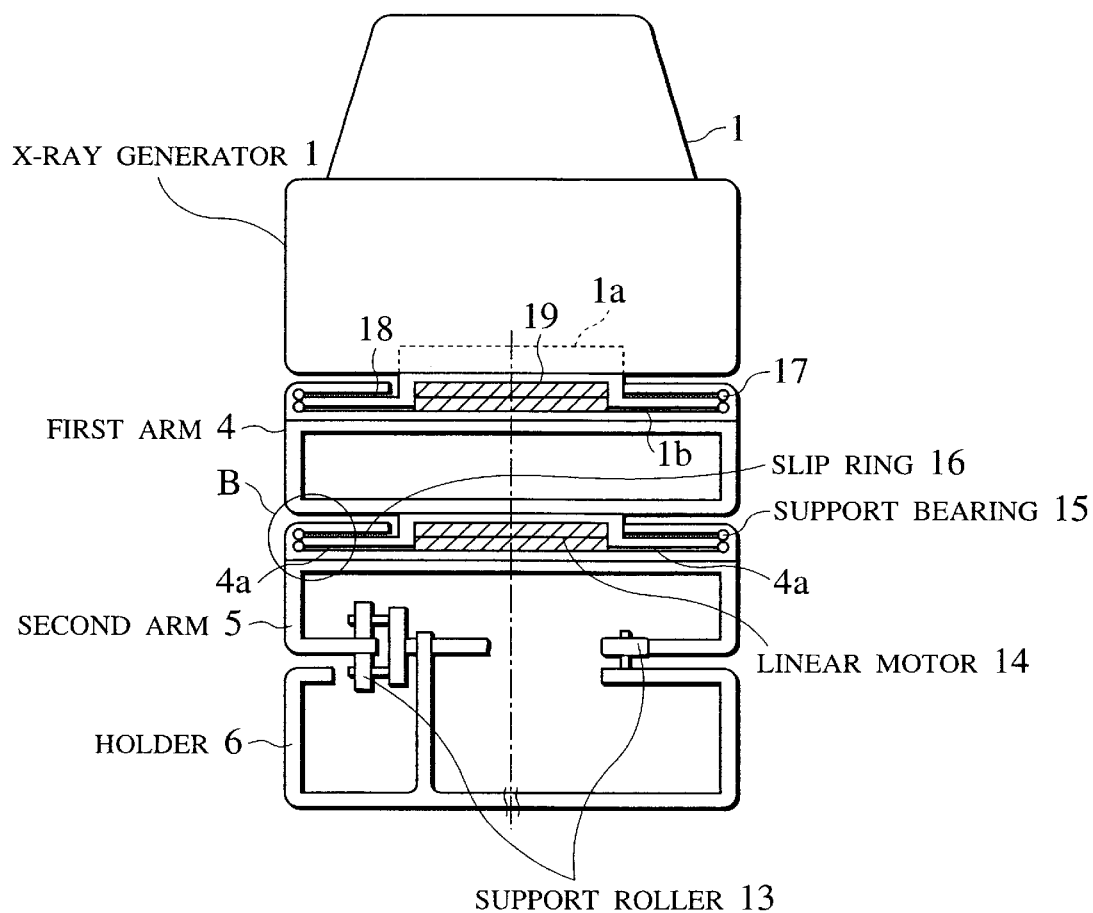
FIG. 7 is a sectional view of FIG. 2 taken along the line VII—VII for explaining a sliding mechanism of the X-ray diagnostic imaging apparatus according to the first embodiment.

Next, a sliding mechanism of the X-ray diagnostic imaging apparatus according to the first embodiment will be explained. FIG. 7 is a sectional view of a portion taken along the line VII—VII in FIG. 2 for showing an outline of a sliding mechanism of the first embodiment.

As shown in FIG. 7, the second arm 5 is held movably by sliding (in a depth direction in FIG. 7) by support rollers 13 provided in the arm holder 6, as is the case with the conventional apparatus. As a driving mechanism for driving the second arm 5, there may be generally used a motor, a reduction gear and a belt.

The first arm 4 is held on the second arm 5 movably by sliding along the second arm 5 (in a depth direction in FIG. 7) by support bearings 15. The support bearings 15 are ball-circulation type bearings built into the second arm 5. The support bearings 15 may be provided over the whole area of the second arm 5, or a plurality of bearings may be provided at divided portions on the second arm 5. A rail 4a of the first arm 4 is held on the support bearings 15 to form a slide track.

When these support bearings 15 are used, it is possible to disperse the load with a plurality of balls so that the arms can be held in a compact structure. In this example, the support bearings 15 are provided at two ends of the second arm 5. However, it is also possible to provide the support bearings 15 at more positions such as four or eight positions.

The first arm 4 is driven by a motor (hereinafter to be referred to as a linear motor 14) of a type having a rotor extended on a plane. A stator of the linear motor 14 is provided at a side of the second arm 5 and a mobile unit is provided at a side of the first arm 4, to carry out a slide operation. Alternatively, the stator and the mobile unit may be provided at opposite positions. As the linear motor can transmit power directly with no contact, it is possible to obtain a high-speed rotation for the sliding. Further, unlike the general motor, the linear motor 14 does not require a reduction gear or a power transmission system. Therefore, it is possible to provide a thin and compact motor.

Figure 8:
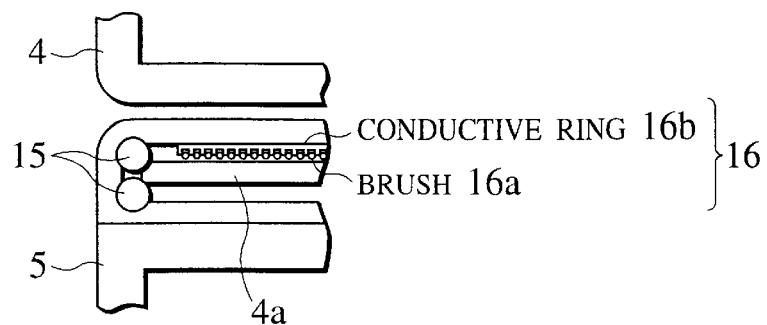
FIG. 8 is an enlarged view of a portion of B in FIG. 7.

When a cable has been absorbed by a sliding operation, this may be entangled at the outside or the cable may be wound up inside. Alternatively, a slip ring may be used. As shown in FIG. 8, which is an enlarged view of a portion of B in FIG. 7, conductive rings 16b corresponding to a required number of channels are provided at the side of the second arm 5, and at the same time, brushes 16a corresponding to the conductive rings 16b are provided in the rail 4a of the first arm 4. In this case, the brushes 16a are provided so that they are always in contact with the conductive rings 16b during a slide rotation of the first arm 4.

According to the above-described sliding structure, the first and second arms 4 and 5 are mutually deviated, and the inner surface of the second arm 5 or the outer surface of the first arm 4 is exposed. However, when the slip ring 16 is disposed inside as shown in FIG. 8, it is possible to prevent a finger from being brought into a direct contact with the slip ring.

In the mean time, a similar structure can also be applied to the mechanism of sliding the X-ray generator 1 along the first arm 4. More specifically, a rail 1b of the rotation support 1a provided at a lower part of the X-ray generator 1 is held to be able to move by sliding on support bearings 17 disposed at an upper part (inside) of the first arm 4, and at the same time, the rail 1b is driven by a linear motor 19 disposed between the rotation support 1a and the first arm 4. A slip ring 18 similar to the one as described above is provided in the rail 1b.

When the support bearings 15 and 17, the linear motors 14 and 19, and the slip rings 15 and 16 are used as described above, it is possible to slide and rotate the first arm 4 and the X-ray generator 1.

According to the first embodiment, it is possible to obtain the following effects.

So long as the C-type arm 3 can support the X-ray detector 2, it becomes possible to reduce the size and weight of the C-type arm 3, with a smaller inertia. Therefore, a subtle positioning in the image pick-up of the subject can also be carried out accurately and promptly. At the same time, it is possible to secure a sufficient work space for an operator 104 without interfering with a field of vision of the operator 104. Further, as it is not necessary to provide a mechanism like a slide movement mechanism in the C-type arm 3, the C-type arm 3 can take various shapes so long as it can support the X-ray detector 2 by making a detour around the subject 7 and the bed 8.

Further, when the X-ray generator 1, the first arm 4 and the second arm 5 are moved by sliding in a state that they are interconnected, it is possible to avoid an interference with the subject and to obtain a sufficient stroke rotation (180 degrees plus X-ray cone beam angle). When image information and angle information are taken in together by rotating these units, and when image data is reconstructed into a three-dimensional image of cone beams, for example, it is possible to obtain various three-dimensional images of the subject as desired. According to the conventional apparatus, it has been difficult to obtain three-dimensional images of practical precision, as it has not been possible to take a sufficient stroke rotation. On the other hand, according to the first embodiment, the X-ray generator 1 directly holds the C-type arm 3, and the first arm 4 and the X-ray generator 1 are structured to be able to slide and rotate. Therefore, the main axis rotation (reference e and reference b in FIG. 2) and the support pillar rotation (reference d in FIG. 2) clinically required can be realized in a simple structure. Thus, it is possible to avoid a space for installing a mechanism that is necessary for obtaining the main axis rotation.

It is also possible to control the stopping of X-rays by interconnection, and to obtain a fan beam for reconstructing three-dimensional image. The first arm and the second arm may be extended to make it possible to rotate the X-ray generator 1 by 360 degrees.

Second Embodiment

An X-ray diagnostic imaging apparatus according to a second embodiment of the present invention will be explained next with reference to FIGS. 9A to 11. Only the points different from those of the first embodiment will be explained in detail.

As shown in FIG. 9A, the X-ray diagnostic imaging apparatus according to the second embodiment is a modification of the first embodiment in that the apparatus includes an arm 20 by extending the first arm 4 by omitting the second arm 5 of the first embodiment shown in FIG. 2.

The arm 20 shown in FIGS. 9A, 9B and 9C forms an arc of one third of a circle, for example. This arm 20 is held by an arm holder 6 so as to be rotatable and slidable along the arm holder 6. The upper surface (inner surface) of the arm 20 holds the X-ray generator 1 rotatably and slidably.

An X-ray diagnostic imaging apparatus 200 having the arm 20 according to the second embodiment can pick up an image of the subject 7 from the front or from the back, by positioning the X-ray generator 1 under the subject 7, as shown in FIG. 9A.

In the case of moving the detector 2 to the right half portion of the subject 7, the arm 20 is slid as shown (by reference a) in FIG. 9B, and the X-ray generator 1 is slid along the arm 20 (as shown by reference c in FIG. 9B). Thus, the X-ray generator 1 is moved in a clockwise circumferential direction.

On the other hand, in the case of moving the detector 2 to the left half portion of the subject 7, the arm 20 is slid as shown (by reference a) in FIG. 9C, and the X-ray generator 1 is slid along the arm 20 (as shown by reference c in FIG. 9C). Thus, the X-ray generator 1 is moved in a counter-clockwise circumferential direction.

According to the X-ray diagnostic imaging apparatus 200 having the above-described structure, it is possible to obtain a sufficient stroke rotation (180degrees plus X-ray cone beam angle) by sliding the X-ray generator 1 and the arm 20 together. Therefore, when image information and angle information are taken in together by rotating the X-ray generator 1 and the arm 20, and when this image information is reconstructed into a three-dimensional image from cone beams, for example, it is possible to obtain desired three-dimensional images of the subject, in a similar manner to the first embodiment.

Further, it is also possible to dispose the arm 20 in parallel with the body axis, by rotating the arm holder 6 with its radial direction as an axis. In this case, it is also possible to rotate the X-ray image pick-up system in a body axial direction, by sliding the X-ray generator 1 along the arm 20. Further, it is also possible to obtain a complex angle setting by combining a rotation of the arm holder 6 and rotations of the arm 20 and the X-ray generator 1.

In the case of observing an inguinal region or a lower extremity of the subject 7, the bed 8 mounted with the subject 7 is moved to the head side, or the arm holder 6 is moved to a body axial direction (as shown by reference i in FIG. 2). In this case, when the X-ray generator 1 is rotated with its radial direction as an axis (as shown by reference e in FIG. 2), if needed, it is possible to avoid an interference between the C-type arm 3 and the subject 7 or the bed 8.

Further, when the up-and-down moving mechanism 11 is expanded or contracted and also when the angle of the X-ray detector 2 and the angle of axial rotation are adjusted by the joint 11a, the X-ray detector 2 can be brought into a close contact with the subject 7.

Next, a sliding mechanism of the X-ray diagnostic imaging apparatus 200 according to the second embodiment will be explained with reference to FIGS. 10 and 11.

Figure 10:
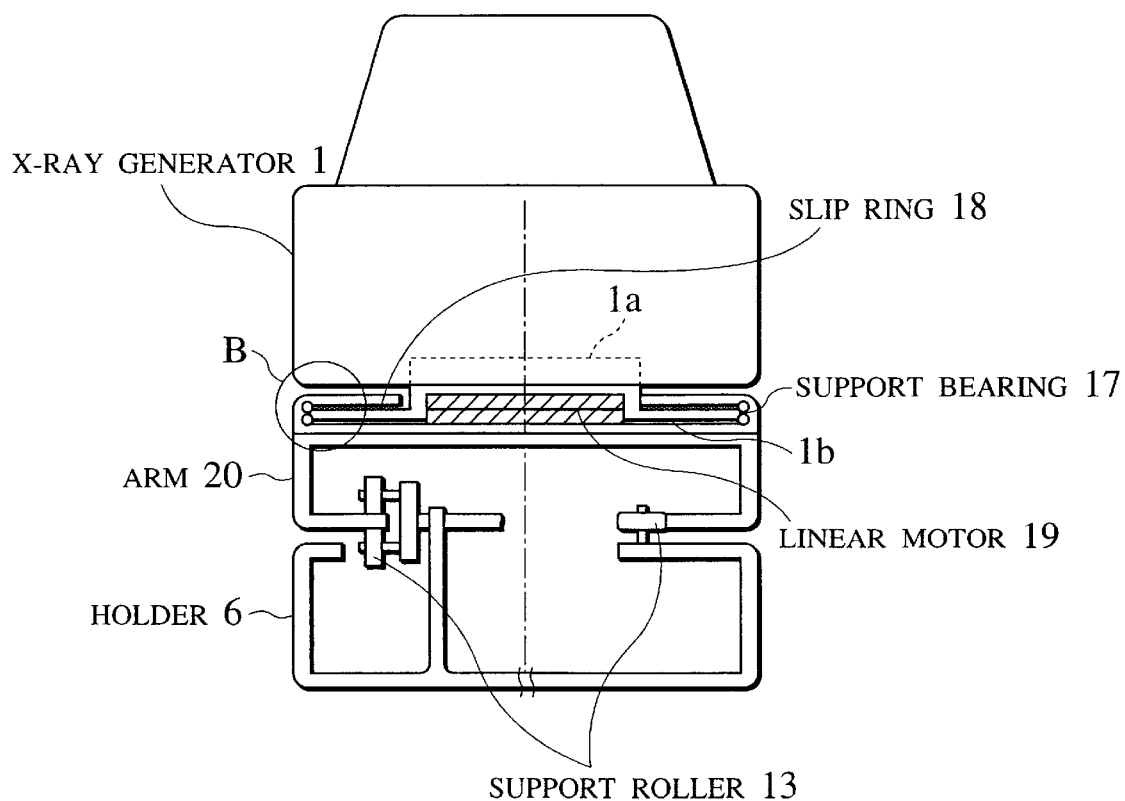
FIG. 10 is a sectional view for explaining a sliding mechanism of the X-ray diagnostic imaging apparatus according to the second embodiment.
Figure 11:
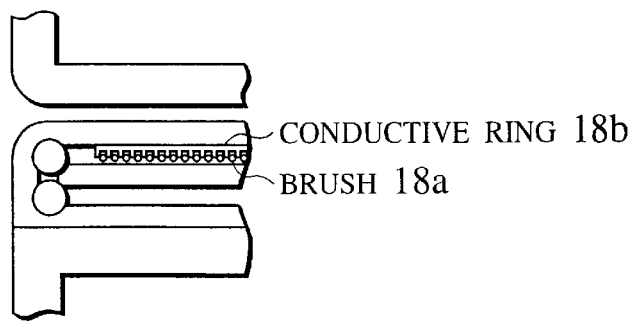
FIG. 11 is an enlarged view of a portion of B in FIG. 10.

FIG. 10 is a sectional view of the X-ray diagnostic imaging apparatus 200 according to the present embodiment.

As shown in FIG. 10, the arm 20 is held by the support rollers 13 provided in the arm holder 6 so that the arm 20 can move by sliding (in a depth direction in FIG. 10), in a manner similar to that of the conventional apparatus. As a driving mechanism for sliding this arm 20, there may be generally used a motor, a reduction gear and a belt.

The rotation support 1a of the X-ray generator 1 is held on the arm 20 movably by sliding along this arm 20 (in a depth direction in FIG. 10) by using support bearings 17. The support bearings 17 are ball-circulation type bearings built into the upper part of the arm 20. The support bearings 17 may be provided over the whole area of the arm 20, or a plurality of bearings may be provided at divided portions on the arm 20. A rail 1b is held on the support bearings 17 to form a slide track.

The X-ray generator 1 is moved by a linear motor 19, for example. More specifically, a stator of the linear motor 19 is provided at a side of the arm 20 and a mobile unit is provided at a side of the rotation support 1a, to carry out a slide operation. Alternatively, the stator and the mobile unit may be provided at opposite positions.

In the second embodiment, it is also possible to use slip rings for control distribution. As shown in FIG. 11, which is an enlarged view of a portion of B in FIG. 10, conductive rings 18b corresponding to a required number of channels are provided at the side of arm 20, and at the same time, brushes 18a corresponding to the conductive rings 18b are provided in the rail 1b of the rotation support 1a. In this case, the brushes 18a are provided so that they are always in contact with the conductive rings 18b during a slide rotation of the rotation support 4.

According to the second embodiment, it is possible to obtain effects similar to those of the first embodiment. Further, as the arm structure can be more simplified, it is possible to reduce the cost of the facility.

Third Embodiments

Next, an X-ray diagnostic imaging apparatus according to a third embodiment of the present invention will be explained with reference to FIGS. 12A, 12B and 12C. Only the points different from those of the preceding embodiments will be explained in detail.

Figure 12A:
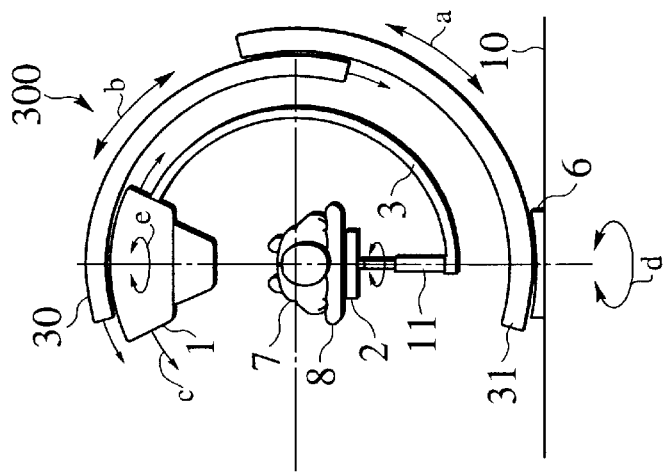
FIGS. 12A to 12C are views for explaining a structure of an X-ray diagnostic imaging apparatus according to a third embodiment of the present invention.

FIG. 12A is a view for explaining a structure of the X-ray diagnostic imaging apparatus 300 according to the third embodiment.

An X-ray diagnostic imaging apparatus 300 according to the third embodiment shown in FIG. 12A is a modification of the first embodiment in that, in place of the first and second arms 4 and 5 of the first embodiment shown in FIG. 2, the apparatus includes a first arm 30 and a second arm 31 that are formed by extending the first and second arms 4 and 5 of the first embodiment.

More specifically, the first and second arms 30 and 31 of the third embodiment form arcs of one third of a circle, for example. The first arm 30 directly holds the X-ray generator 1. The second arm 31 slidably holds the first arm 30 (as shown by reference b in FIG. 12A), and is also slidably supported by the arm holder 6 (as shown by reference a in FIG. 12A). The arm holder 6 is embedded into the surface of the floor 10 rotatably around a vertical axis D.

Next, the operation of the X-ray diagnostic imaging apparatus 300 according to the third embodiment will be explained.

In an initial status shown in FIG. 12A, the first and second arms 30 and 31 are superimposed together on the arm holder 6 in a stationary status. The X-ray generator 1 is stationary at the right end of the first arm 30. In this initial status, the X-ray generator 1 is positioned below the subject 7, and the X-ray detector 2 is positioned above the subject 7 so that both X-ray generator 1 and the X-ray detector 2 are oppositely disposed to sandwich the subject 7 therebetween.

Figure 12B:
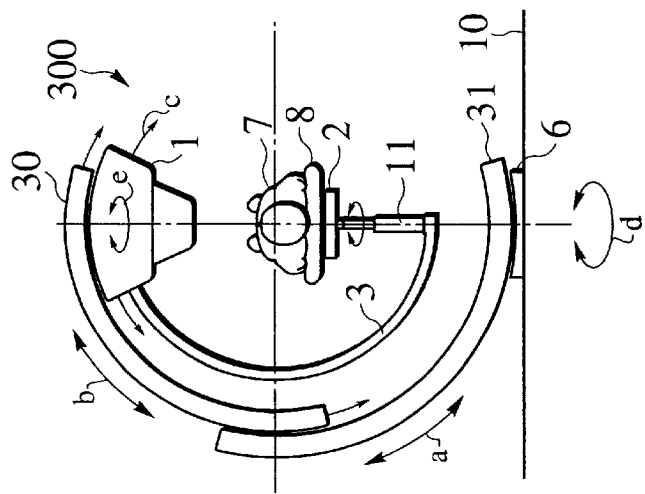

In the case of moving the detector 2 to the right half portion of the subject 7, the second arm 31 and the first arm 30 are slid respectively as shown (by reference a and reference b) in FIG. 12B, and the X-ray generator 1 is slid along the first arm 30 (as shown by reference c in FIG. 12B). Thus, the X-ray generator 1 is moved in a clockwise circumferential direction.

Figure 12C:
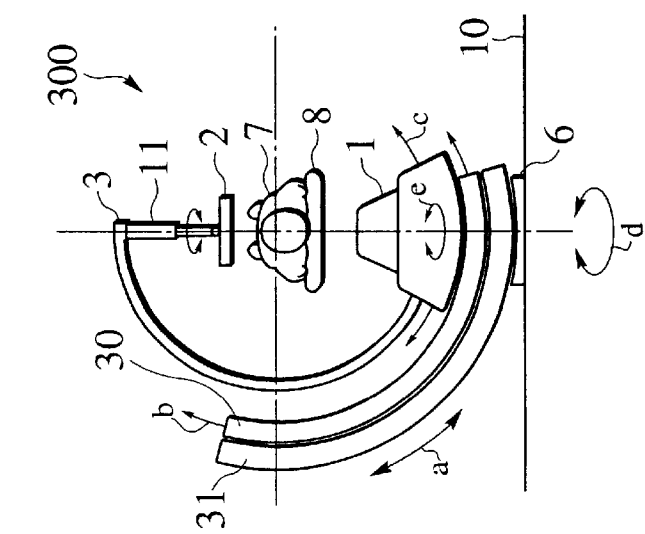

On the other hand, in the case of moving the detector 2 to the left half portion of the subject 7, the second arm 31 and the first arm 30 are slid respectively as shown (by reference a and reference b) in FIG. 12C, and the X-ray generator 1 is slid along the first arm 30 (as shown by reference c in FIG. 12C). Thus, the X-ray generator 1 is moved in a counterclockwise circumferential direction.

According to the X-ray diagnostic imaging apparatus 300 of the above-described structure, it is possible to obtain a stroke rotation of 360 degrees or above by interconnecting the sliding of the X-ray generator 1, the first arm 30 and the second arm 31. Therefore, when image information and angle information are taken in together by rotating these units, and when this image information is reconstructed into a three-dimensional image from cone beams, for example, it is possible to obtain desired three-dimensional images of the subject.

Further, in the third embodiment, it is also possible to dispose the first and second arms 30 and 31 in parallel with the body axis, by rotating the arm holder 6 with its radial direction as an axis. In this case, it is also possible to rotate the X-ray image pick-up system in a body axial direction, by sliding the first arm 30 and the X-ray generator 1 along the second arm 31. Further, it is also possible to obtain a complex angle setting by combining a rotation of the arm holder 6 and rotations of the first and second arms 30 and 31 and the X-ray generator 1.

In the case of observing an inguinal region or a lower extremity of the subject 7, the bed 8 mounted with the subject 7 is moved to the head side, or the arm holder 6 is moved to a body axial direction (as shown by reference i in FIG. 2) before irradiating X-rays onto the subject 7. In this case, when the X-ray generator 1 is rotated with its radial direction as an axis (as shown by reference e in FIG. 2), if needed, it is possible to avoid an interference between the C-type arm 3 and the subject 7 or the bed 8.

Further, when the up-and-down moving mechanism 11 is expanded or contracted and also when the angle of the X-ray detector 2 and the angle of axial rotation are adjusted by the joint 11a, the X-ray detector 2 can be brought into a close contact with the subject 7.

According to the third embodiment, it is possible to obtain images of the subject in a larger stroke rotation, in addition to the effects obtained by the preceding embodiments.

Fourth Embodiment

Next, an X-ray diagnostic imaging apparatus according to a fourth embodiment of the present invention will be explained with reference to FIG. 13. Only the points different from those of the preceding embodiments will be explained in detail.

Figure 13:
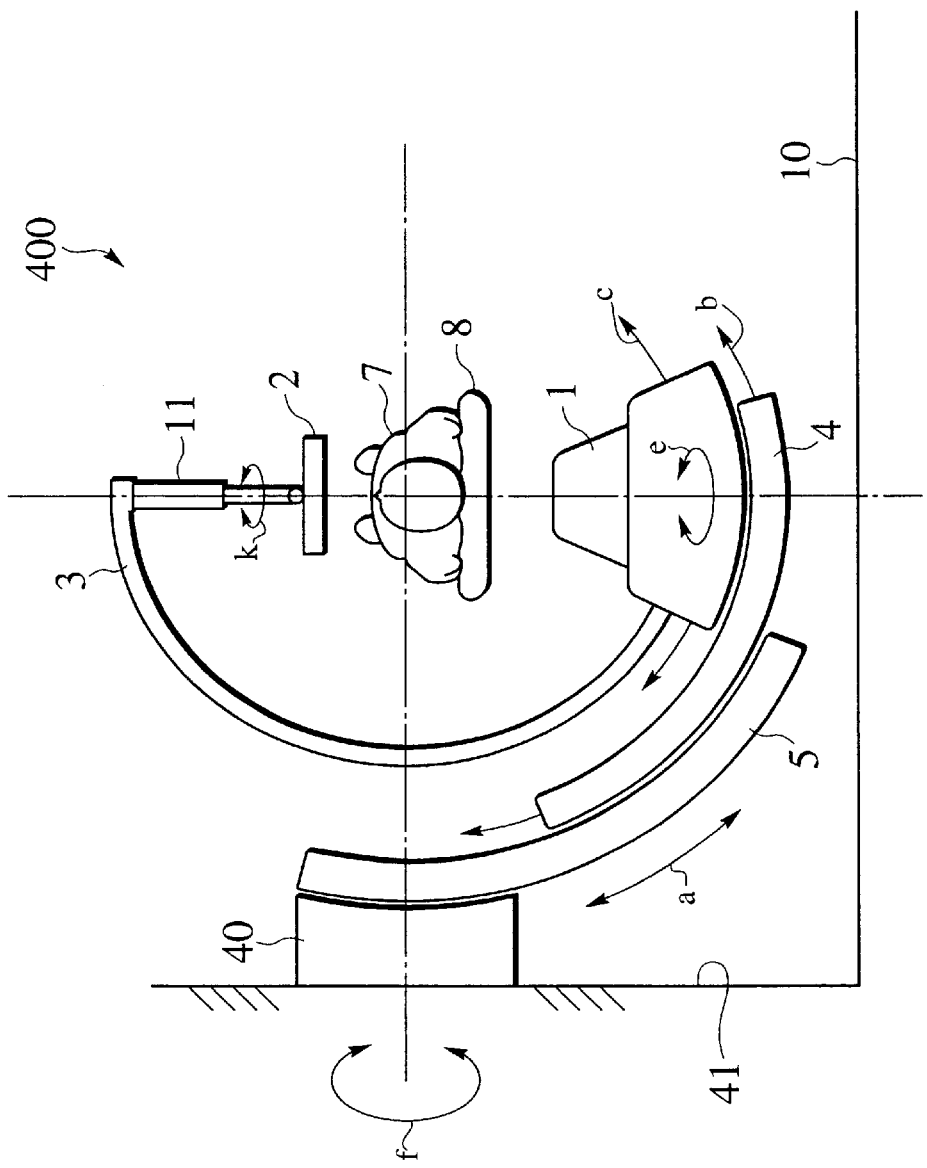
FIG. 13 is a front view of an X-ray diagnostic imaging apparatus according to a fourth embodiment of the present invention as viewed from the head side of a subject.

FIG. 13 is a view for explaining an X-ray diagnostic imaging apparatus 400 according to the fourth embodiment. The X-ray diagnostic imaging apparatus 400 according to the fourth embodiment is a modification of the first embodiment in that, in place of the arm holder 6 of the first embodiment shown in FIG. 2, the apparatus includes an arm holder 40 provided rotatably on a side wall 41 at the side of the subject 7.

More specifically, the first and second arms 4 and 5 of the fourth embodiment form arcs of a quarter of a circle, for example. The first arm 4 directly holds the X-ray generator 1. The second arm 5 slidably holds the first arm 4 (as shown by reference b in FIG. 13), and is also slidably supported by the arm holder 40 (as shown by reference a in FIG. 13). The arm holder 40 is embedded into the surface of a side wall 41 rotatably around a horizontal axis f. At the same time, the arm holder 40 is structured to be able to move forward and backward from the side wall and slide along the side wall 41.

According to the X-ray diagnostic imaging apparatus 400 having the above-described structure, the first arm 4 and the second arm 5 are slid respectively as shown (by reference a and reference b) in FIG. 13, and the X-ray generator 1 is slid along the first arm 4 (as shown by reference c in FIG. 13). Thus, the X-ray generator 1 can be moved in a circumferential direction around the body axis of the subject 7. It is also possible to rotate the X-ray detector 2 in a body axial direction of the subject 7, by moving the bed 8 or the arm holder 40 in a forward or backward direction. Further, when the up-and-down moving mechanism 11 is expanded or contracted and also when the angle of the X-ray detector 2 and the angle of axial rotation are adjusted by the joint 11a, the X-ray detector 2 can be brought into a close contact with the subject 7.

According to the fourth embodiment, it is possible to obtain effects similar to those of the preceding embodiments.

Fifth Embodiment

Figure 14:
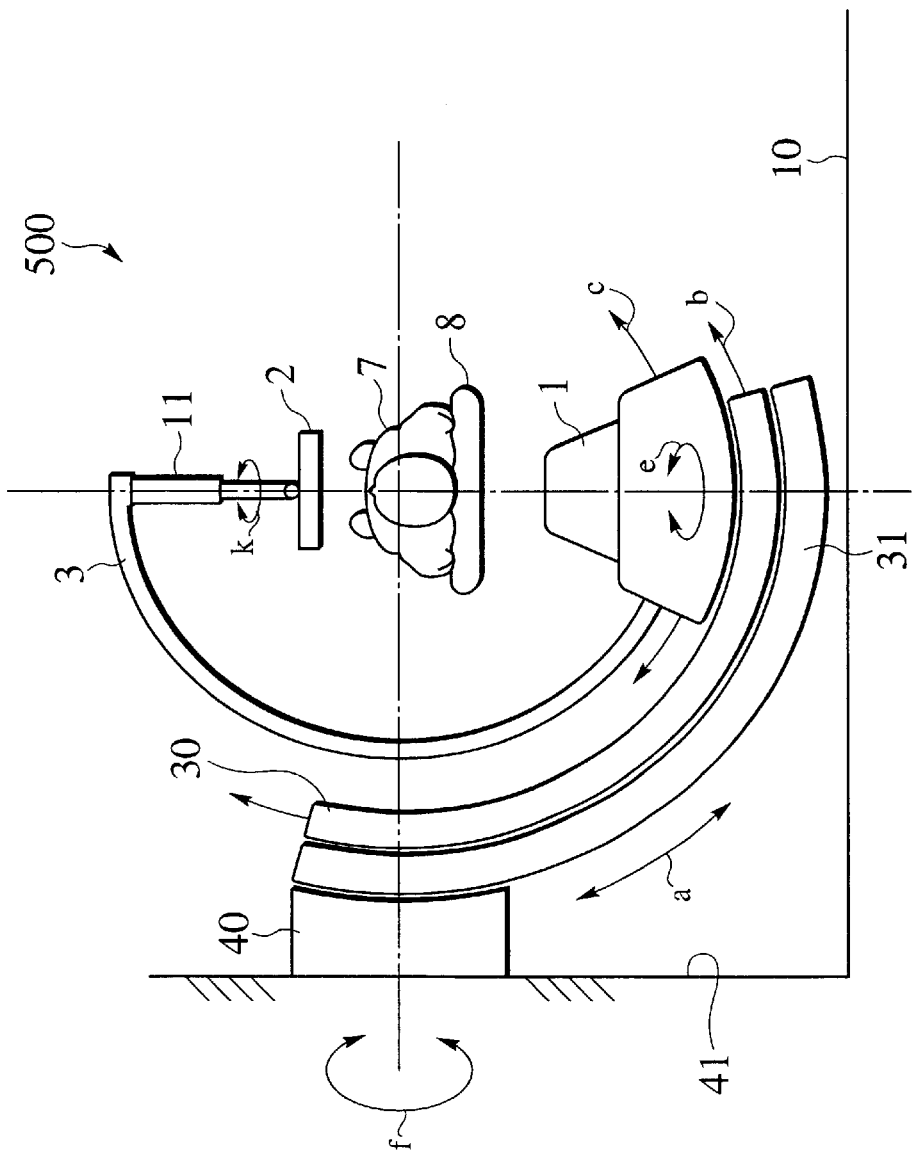
FIG. 14 is a front view of an X-ray diagnostic imaging apparatus according to a fifth embodiment of the present invention as viewed from the head side of a subject.

Next, an X-ray diagnostic imaging apparatus according to a fifth embodiment of the present invention will be explained with reference to FIG. 14. Only the points different from those of the preceding embodiments will be explained in detail. FIG. 14 is a view for explaining an X-ray diagnostic imaging apparatus 500 according to the fifth embodiment.

The fifth embodiment is a modification of the fourth embodiment in that the first and second arms 4 and 5 of the fourth embodiment shown in FIG. 13 have been replaced with the first and second arms 30 and 31 of the third embodiment shown in FIG. 12A.

More specifically, the first and second arms 30 and 31 of the fifth embodiment form arcs of one third of a circle, for example. The first arm 30 directly holds the X-ray generator 1. The second arm 31 slidably holds the first arm 30 (as shown by reference b in FIG. 14), and is also slidably supported by the arm holder 40 (as shown by reference a in FIG. 14). In a manner similar to that of the fourth embodiment, the arm holder 40 is embedded into the surface of the side wall 41 rotatably around the horizontal axis f. At the same time, the arm holder 40 is structured to be able to move forward and backward from the side wall 41 and slide along the side wall 41.

According to the X-ray diagnostic imaging apparatus 500 having the above-described structure, the first arm 30 and the second arm 31 are slid respectively as shown (by reference a and reference b) in FIG. 14, and the X-ray generator 1 is slid along the first arm 30 (as shown by reference c in FIG. 14). Thus, the X-ray generator 1 can be moved in a circumferential direction around the body axis of the subject.

It is also possible to rotate the X-ray detector 2 in a body axial direction of the subject 7, by moving the arm holder 40 or the bed 8 in a forward or backward direction. Further, when the up-and-down moving mechanism 11 is expanded or contracted and also when the angle of the X-ray detector 2 and the angle of axial rotation are adjusted by the joint 11*a*, the X-ray detector 2 can be brought into a close contact with the subject 7.

Sixth Embodiment

Figure 15:
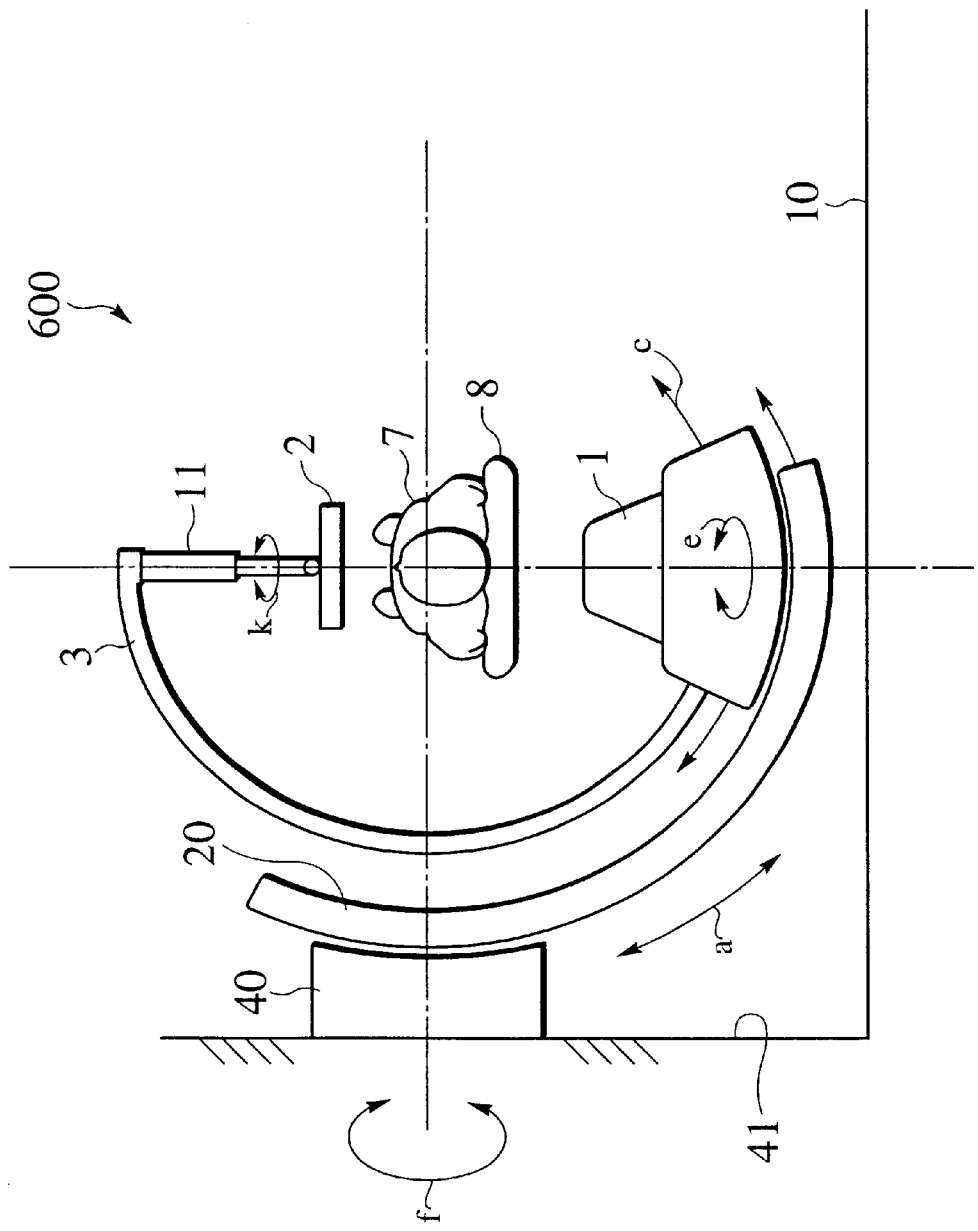
FIG. 15 is a front view of an X-ray diagnostic imaging apparatus according to a sixth embodiment of the present invention as viewed from the head side of a subject.

Next, an X-ray diagnostic imaging apparatus according to a sixth embodiment of the present invention will be explained with reference to FIG. 14. Only the points different from those of the preceding embodiments will be explained in detail. FIG. 15 is a view for explaining an X-ray diagnostic imaging apparatus 600 according to the sixth embodiment.

The sixth embodiment is a modification of the fourth embodiment in that the first and second arms 4 and 5 of the fourth embodiment shown in FIG. 13 have been replaced with the arm 20 of the second embodiment shown in FIG. 9A.

More specifically, the arm 20 forms an arc of one third of a circle, for example. The arm 20 directly holds the X-ray generator 1 slidably (as shown by reference c in FIG. 15) and rotatably (as shown by reference e in FIG. 15). At the same time, the arm 20 is also slidably supported by the arm holder 40 (as shown by reference a in FIG. 15). The arm holder 40 is embedded into the surface of the side wall 41 rotatably around the horizontal axis f.

According to the X-ray diagnostic imaging apparatus 600 having the above-described structure, it is possible to move the X-ray generator 1 in a circumferential direction around the body axis of the subject, by sliding the arm 20 (as shown by reference a in FIG. 15) and by sliding the X-ray generator 1 along the arm 20 (as shown by reference c in FIG. 15). Further, when the up-and-down moving mechanism 11 is expanded or contracted and also when the angle of the X-ray detector 2 and the angle of axial rotation are adjusted by the joint 11*a*, the X-ray detector 2 can be brought into a close contact with the subject 7.

Seventh Embodiment

Next, an X-ray diagnostic imaging apparatus according to a seventh embodiment of the present invention will be explained with reference to FIG. 16. Only the points different from those of the preceding embodiments will be explained in detail. FIG. 20 is a view for explaining an X-ray diagnostic imaging apparatus 700 according to the seventh embodiment.

The seventh embodiment is a modification of the fourth embodiment in that the first and second arms 4 and 5 and the arm holder 40 of the fourth embodiment shown in FIG. 13 have been replaced by an arm 70.

More specifically, the arm 70 forms an arc of a quarter of a circle, for example, and is integrally formed with the arm holder. This arm 70 does not have the above-described sliding mechanism for the arm holder for holding the arms, and carries out only a rotation around the horizontal axis (as shown by reference f in FIG. 16).

Figure 16:
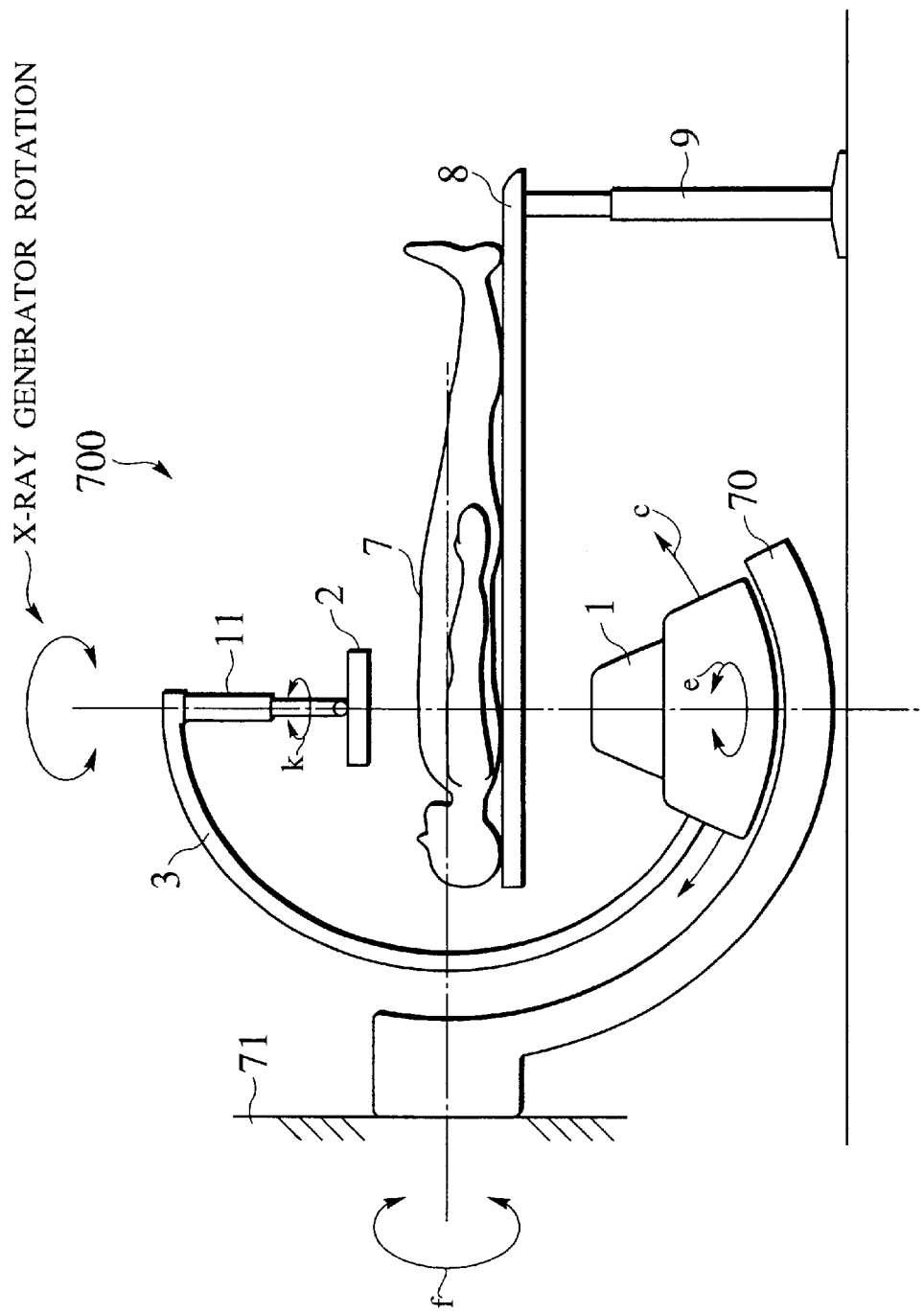
FIG. 16 is a side view of an X-ray diagnostic imaging apparatus according to a seventh embodiment of the present invention as viewed from the side of a subject.

The arm 70 directly holds the X-ray generator 1 slidably (as shown by reference c in FIG. 16) and rotatably (as shown by reference e in FIG. 16). At the same time, the arm 70 is embedded into a side wall 71 provided perpendicularly to a body axial direction of the subject 7 (that is, near the head of the subject 7) rotatably around an axis f. Further, the arm holder 70 is structured to be able to move forward and backward from the side wall 71 and slide along the side wall 71.

According to the X-ray diagnostic imaging apparatus 700 having the above-described structure, it is possible to rotate the X-ray image pick-up system in a body axial direction of the subject, by sliding the X-ray generator 1 along the arm 70 (as shown by reference c in FIG. 16). Further, when the up-and-down moving mechanism 11 is expanded or contracted and also when the angle of the X-ray detector 2 and the angle of axial rotation are adjusted by the joint 11*a*, the X-ray detector 2 can be brought into a close contact with the subject 7.

Eighth Embodiment

Figure 17:
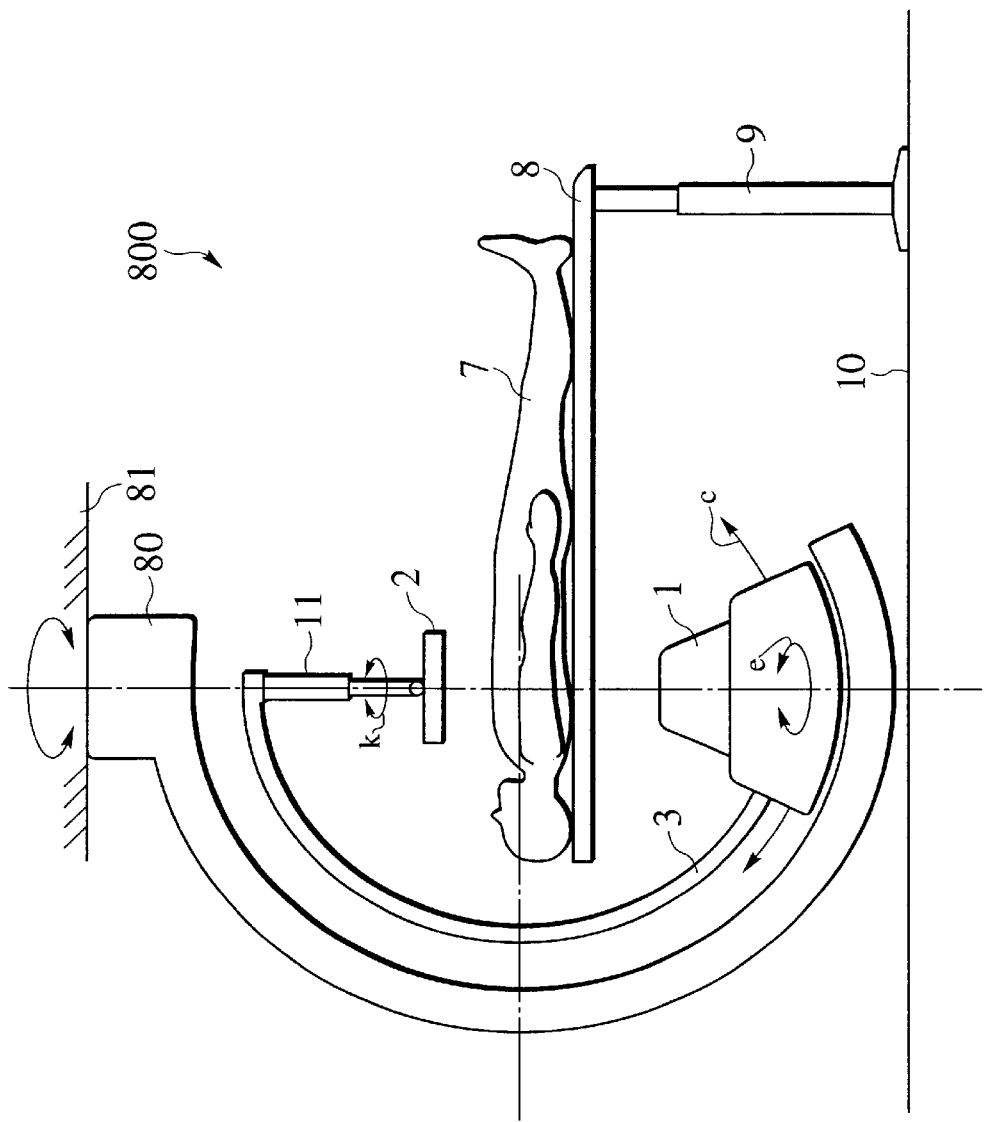
FIG. 17 is a side view of an X-ray diagnostic imaging apparatus according to an eighth embodiment of the present invention as viewed from the side of a subject.

Next, an X-ray diagnostic imaging apparatus according to an eighth embodiment of the present invention will be explained with reference to FIG. 17. Only the points different from those of the preceding embodiments will be explained in detail. FIG. 17 is a view for explaining an X-ray diagnostic imaging apparatus 800 according to the eighth embodiment.

The eighth embodiment is a modification of the seventh embodiment in that the arm 70 shown in FIG. 16 has been replaced by an arm 80 shown in FIG. 17.

More specifically, the arm 80 forms an arc of 180 degrees or more, and is integrally formed with the arm holder. The arm 80 directly holds the X-ray generator 1 slidably (as shown by reference c in FIG. 17) and rotatably (as shown by reference e in FIG. 17). At the same time, the arm 80 is embedded into a ceiling 81 rotatably on the ceiling.

According to the X-ray diagnostic imaging apparatus 800 having the above-described structure, it is possible to rotate the X-ray image pick-up system in a body axial direction of the subject, by moving the X-ray generator 1 in a direction along the arc of the arm 80 by sliding the X-ray generator 1 along the arm 8 (as shown by reference c in FIG. 17). It is also possible to dispose the arm 80 in a direction orthogonal with the body axis of the subject 7 by rotating the arm 80. Further, when the up-and-down moving mechanism 11 is expanded or contracted and also when the angle of the X-ray detector 2 and the angle of axial rotation are adjusted by the joint 11*a*, the X-ray detector 2 can be brought into a close contact with the subject 7.

Ninth Embodiment

Figure 18:
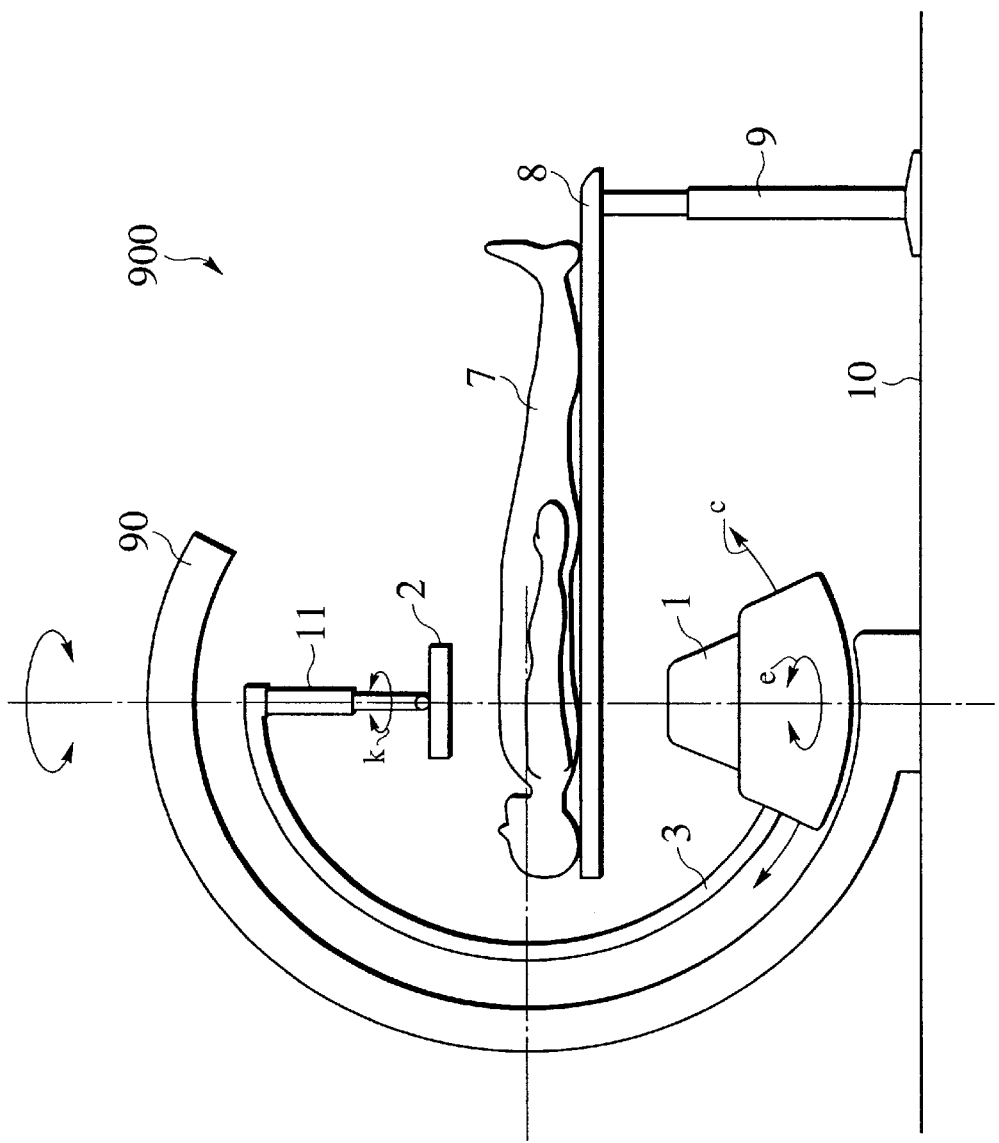
FIG. 18 is a side view of an X-ray diagnostic imaging apparatus according to a ninth embodiment of the present invention as viewed from the side of a subject.

Next, an X-ray diagnostic imaging apparatus according to a ninth embodiment of the present invention will be explained with reference to FIG. 18. Only the points different from those of the preceding embodiments will be explained in detail. FIG. 18 is a view for explaining an X-ray diagnostic imaging apparatus 900 according to the ninth embodiment.

The ninth embodiment is a modification of the eighth embodiment in that the arm 80 shown in FIG. 17 has been replaced with an arm 90 shown in FIG. 18.

More specifically, the arm 90 forms an arc of 180 degrees or more, for example, and is integrally formed with the arm holder. The arm 90 directly holds the X-ray generator 1 slidably (as shown by reference c in FIG. 18) and rotatably (as shown by reference e in FIG. 18). At the same time, the arm 90 is embedded into a wall 10 movably in all directions by sliding on the wall 10.

According to the X-ray diagnostic imaging apparatus 900 having the above-described structure, it is possible to tilt the X-ray image pick-up system in a body axial direction by slide moving the X-ray generator 1 along the arm 90. It is also possible to dispose the arm 90 in a direction orthogonal with the body axis of the subject 7 by rotating the arm 90 with its radial direction as an axis. In this case, when the X-ray generator 1 is slid along the arm 90, it becomes possible to pick up images over a sufficient stroke angle (180 degrees plus X-ray cone beam angle) around the body axis of the subject 7. Therefore, it is possible to obtain desired three-dimensional images of the subject.

Tenth Embodiment

Figure 19:
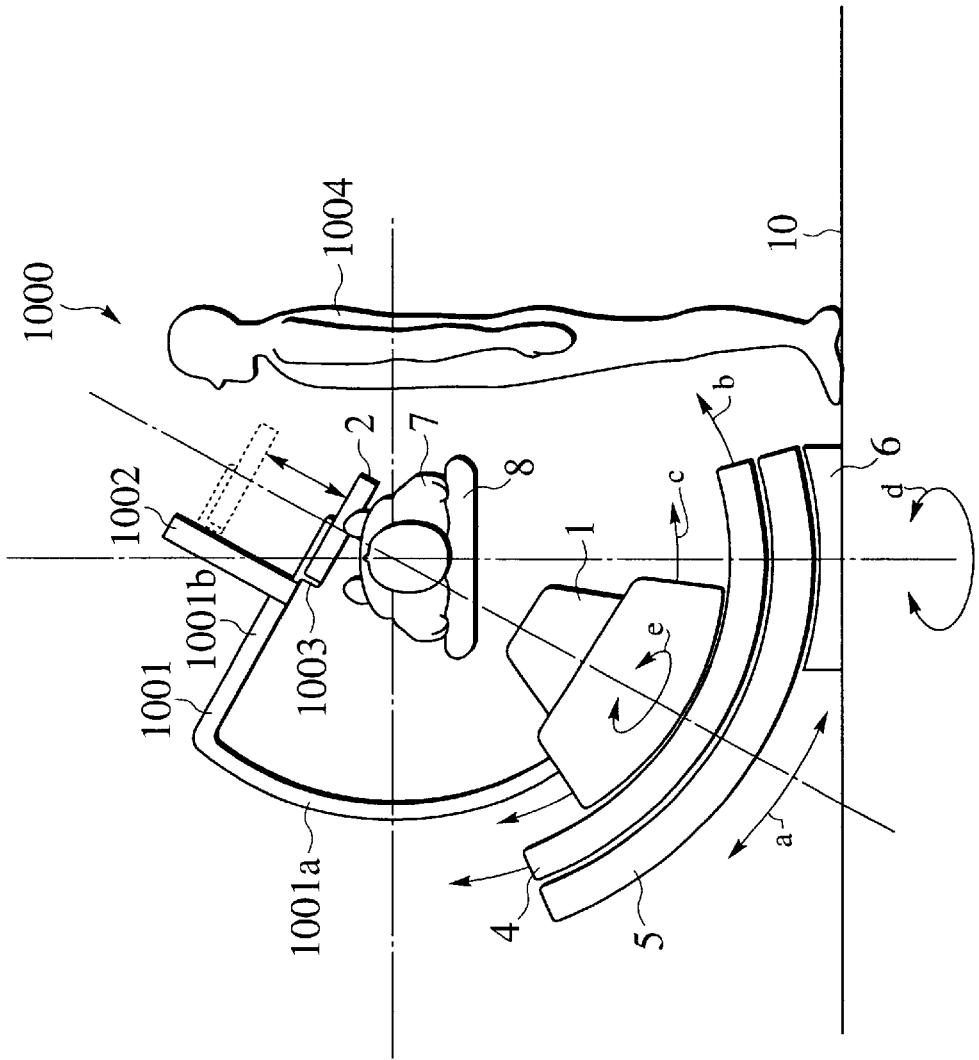
FIG. 19 is a front view of an X-ray diagnostic imaging apparatus according to a tenth embodiment of the present invention as viewed from the head side of a subject.

Next, an X-ray diagnostic imaging apparatus according to a tenth embodiment of the present invention will be explained with reference to FIG. 19. Only the points different from those of the preceding embodiments will be explained in detail. FIG. 19 is a view for explaining an X-ray diagnostic imaging apparatus 1000 according to the tenth embodiment.

The tenth embodiment is a modification of the first embodiment in that the C-type arm 3 of the first embodiment shown in FIG. 2 has been replaced by a modified arm 1001 that has a modified shape of the C-type arm 3.

More specifically, the modified arm 1001 is structured by an arc-shaped part 1001a forming an arc shape of a quarter, for example, a linear part 1001b curved in a radial direction of the arm, and an up-and-down moving part 1002 provided in a direction orthogonal with the linear part 1001. This modified arm 1001 has its end fixedly held by the X-ray generator 1, so that up-and-down driving directions of the up-and-down moving part 1002 orthogonal with the linear part 1001b become parallel with X-ray beams irradiated from the X-ray generator 1. The up-and-down moving part 1002 holds the X-ray detector 2 movably in up and down directions in such a way that the move of the X-ray detector 2 becomes orthogonal with the up-and-down move direction of the up-and-down part 1002. With this arrangement, the X-ray detector 2 moves toward and backward from the X-ray generator 1, thereby changing a distance between the X-ray detector 2 and the X-ray generator 1.

According to the X-ray diagnostic imaging apparatus 1000 having the above-described structure, the first arm 4 and the second arm 5 are slid respectively as shown (by reference a and reference b in FIG. 19), and the X-ray generator 1 is slid along the first arm 4 (as shown by reference c in FIG. 19). Thus, the X-ray generator 1 can be moved in a circumferential direction around the body axis of the subject 7.

It is also possible to dispose the first and second arms 4 and 5 so as to be in parallel with the body axis, by rotating the arm holder 6 with its radial direction as an axis. In this case, it is also possible to tilt the X-ray image pick-up system to a body axial direction, by sliding the first arm 4 and the X-ray generator 1 along the second arm 5. Further, it is also possible to obtain a complex angle setting by combining a rotation of the arm holder 6 and rotations of the first and second arms 4 and 5 and the X-ray generator 1.

In the case of observing an inguinal region or a lower extremity of the subject 7, the bed 8 mounted with the subject 7 is moved to the head side, or the arm holder 6 is moved to a body axial direction before irradiating X-rays onto the subject 7. In this case, when the X-ray generator 1 is rotated with its radial direction as an axis (as shown by reference e in FIG. 19), if needed, it is possible to avoid an interference between the modified arm 1001 and the subject 7 or the bed 8. Further, when the up-and-down moving mechanism 1002 is moved and also when the angle of the X-ray detector 2 and the angle of axial rotation are adjusted by the joint 11a, the X-ray detector 2 can be brought into a close contact with the subject 7.

According to the tenth embodiment, as the modified arm 1001 is bent in a radial direction in the middle, it is possible to reduce the space required for a rotation as compared with the case where the C-type arm 3 shown in FIG. 3 is used. Therefore, the arm will not be in contact with an operator 1004 even when the operator 1004 is close to the subject 7. As a result, it is possible to secure the safety of the operator 1004 and to improve the work efficiency of the operator by expanding the work space for the operator 1004.

The above-described embodiments can be implemented individually, or they can also be implemented in a suitable combination.

In summary, according to the X-ray diagnostic imaging apparatus according to the present invention, in a radiation diagnostic imaging apparatus having an X-ray generator and an X-ray detector held by an arm/arms, the X-ray detector is fixedly held by the arm extended from the X-ray generator, and a holder holds the X-ray generator itself slidably and rotatably. Therefore, there are effects that it is possible to reduce the weight of the arm and the driving mechanism so that an accurate image pick-up position can be set, that it is possible to avoid an interference with the subject, and that it is possible to easily obtain various three-dimensional volume images without losing access to the subject.

Furthermore, there is an effect that it is possible to reduce the installation space of the apparatus because of the reduction in size and weight of the apparatus, which improves the operator's operation.

It is to be noted that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. An X-ray diagnostic imaging apparatus for irradiating X-rays onto a subject under examination and picking up an image of the subject by detecting the X-rays transmitted through the subject, the X-ray diagnostic imaging apparatus comprising:

an X-ray generator for irradiating X-rays onto the subject;

an X-ray detector for taking in an X-ray image formed by the X-rays irradiated by the X-ray generator onto the subject and transmitted through the subject, said X-ray detector comprising a two-dimensional planar array of a plurality of X-ray detecting elements for converting X-rays into electric charge signals and for storing these charge signals;

an arm extended from the X-ray generator to make a detour around the subject, said X-ray detector being equipped at one end of said arm; and a holder for movably holding the X-ray generator, wherein said X-ray generator slides along the holder.

2. The X-ray diagnostic imaging apparatus according to claim 1, wherein the X-ray generator is provided on the holder rotatably with a direction of the irradiation of the X-rays as an axis.

3. The X-ray diagnostic imaging apparatus according to claim 1, wherein the X-ray generator is provided on the holder slidably along an inner surface of the holder.

4. The X-ray diagnostic imaging apparatus according to claim 1, wherein the holder has an arc shape, and the X-ray generator is provided on the holder slidably along the arc of the holder.

5. The X-ray diagnostic imaging apparatus according to claim 1, wherein the holder is supported by a supporting base rotatably on the supporting base.

6. The X-ray diagnostic imaging apparatus according to claim 1, wherein the holder is supported by a supporting base slidably along the arc of the holder.

7. The X-ray diagnostic imaging apparatus according to claim 6, wherein the supporting base is provided movably.

8. The X-ray diagnostic imaging apparatus according to claim 1, wherein the holder includes:
an arc-shaped first holder for movably holding the X-ray generator; and
an arc-shaped second holder for slidably supporting the first holder along the arc of the first holder.

9. The X-ray diagnostic imaging apparatus according to claim 1, wherein the X-ray detector is held on the arm so that an angle formed by the X-ray detector and the X-ray generator can be changed.

10. The X-ray diagnostic imaging apparatus according to claim 1, wherein the X-ray detector is held on the arm so that a distance between the X-ray detector and the X-ray generator can be changed.

11. The X-ray diagnostic imaging apparatus according to claim 1, wherein the X-ray detector is held on the arm so that the X-ray detector can rotate in an axial rotational direction of an X-ray axis formed by a line connecting between the X-ray generator and the X-ray detector.

12. An X-ray diagnostic imaging apparatus for irradiating X-rays onto a subject under examination and picking up an image of the subject by detecting the X-rays transmitted through the subject, the X-ray diagnostic imaging apparatus comprising:

an X-ray generator for irradiating X-rays onto the subject;
an X-ray detector for taking in an X-ray image formed by the X-rays irradiated by the X-ray generator onto the subject and transmitted through the subject;
an arm extended from the X-ray generator to make a detour around the subject, said X-ray detector being equipped on one end of said arm;
an arc-shaped first holder for movably holding the X-ray generator; and
an arc-shaped second holder for slidably supporting the first holder along the arc of the first holder, wherein said X-ray generator slides along said arc-shaped first holder and said arc-shaped second holder slides on a supporting base.

13. An X-ray diagnostic imaging apparatus for irradiating X-rays onto a subject under examination and picking up an image of the subject by detecting the X-rays transmitted through the subject, the X-ray diagnostic imaging apparatus comprising:

an X-ray generator for irradiating X-rays onto the subject;
an X-ray detector for taking in an X-ray image formed by the X-rays irradiated by the X-ray generator onto the subject and transmitted through the subject;
an arm extended from the X-ray generator to make a detour around the subject, said X-ray detector being equipped on one end of said arm; and
an arc-shaped holder for movably holding the X-ray generator, wherein said X-ray generator slides along said arc-shaped holder and said arc-shaped holder slides on a supporting base.

14. The X-ray diagnostic imaging apparatus according to claim 13, wherein said arc-shaped holder slides on a supporting base.

15. The X-ray diagnostic imaging apparatus according to claim 14, wherein a slide movement mechanism for sliding said X-ray generator is only provided in said arc-shaped holder.

16. The X-ray diagnostic imaging apparatus according to claim 14, wherein a slide movement mechanism for sliding said X-ray generator is only provided in said arc-shaped holder.

17. The X-ray diagnostic imaging apparatus according to claim 14, wherein said arc-shaped holder is out of contact with said arm which has said X-ray generator on its one end and said X-ray detector on the other end.

18. The X-ray diagnostic imaging apparatus according to claim 14, wherein said arc-shaped holder is out of contact with said arm which has said X-ray generator at its one end and said X-ray detector at the other end.

* * * * *